United States Patent
Peng et al.

(10) Patent No.: US 10,346,719 B2
(45) Date of Patent: Jul. 9, 2019

(54) MAGNETIC RESONANCE IMAGE ANALYSIS METHOD AND METHOD FOR EVALUATING THE RISKS OF RADIOTHERAPY

(71) Applicant: TAIPEI VETERANS GENERAL HOSPITAL, Taipei (TW)

(72) Inventors: Syu-Jyun Peng, Hsinchu County (TW); Cheng-Chia Lee, Taipei (TW); Huai-Che Yang, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 65 days.

(21) Appl. No.: 15/861,691

(22) Filed: Jan. 4, 2018

(65) Prior Publication Data
US 2019/0087688 A1   Mar. 21, 2019

(30) Foreign Application Priority Data
Sep. 19, 2017   (TW) .............................. 106132128 A

(51) Int. Cl.
*G06K 9/00*   (2006.01)
*A61N 5/00*   (2006.01)
(Continued)

(52) U.S. Cl.
CPC ............ *G06K 9/6224* (2013.01); *A61B 5/055* (2013.01); *A61N 5/1071* (2013.01);
(Continued)

(58) Field of Classification Search
USPC ....... 382/100, 103, 128, 134, 154, 155, 162, 382/168, 173, 181, 209, 220, 232, 254,
(Continued)

(56) References Cited

U.S. PATENT DOCUMENTS 9,412,163 B2 *   8/2016   Peng ......................... G06T 7/11
9,870,614 B1 *   1/2018   Chou ...................... A61B 5/055
(Continued)

FOREIGN PATENT DOCUMENTS

CN   103345753 A   10/2013
CN   103549953 A    2/2014
(Continued)

*Primary Examiner* — Seyed H Azarian
(74) *Attorney, Agent, or Firm* — CKC & Partners Co., LLC

(57) ABSTRACT

The present disclosure provides a magnetic resonance (MR) image analysis method for a patient who underwent radiotherapy. The method includes the steps: receiving an MR image set of a patient and a dose map of a radiotherapy plan; converting the dose intensity distribution of the dose map into the relative spatial positions in the MR image set; selecting a radiation dose and a radiation exposure region, wherein the radiation exposure region has radiation intensity being equal to or higher than the radiation dose; using the radiation exposure region to determine a region of interest (ROI) in the MR image set; classifying the voxels inside the ROI of the MR image set into different clusters according to the grayscale values of the voxels inside the ROI; and calculating the volume or ratios of the different clusters inside the ROI. The present disclosure also provides a method for evaluating risks of radiotherapy.

17 Claims, 22 Drawing Sheets

(51) Int. Cl.
  *G06K 9/62* (2006.01)
  *G06T 7/00* (2017.01)
  *G06T 7/11* (2017.01)
  *G06T 7/174* (2017.01)
  *G06T 7/168* (2017.01)
  *G06T 7/38* (2017.01)
  *A61N 5/10* (2006.01)
  *A61B 5/055* (2006.01)

(52) U.S. Cl.
  CPC ......... *A61N 5/1084* (2013.01); *G06K 9/6223* (2013.01); *G06T 7/0014* (2013.01); *G06T 7/11* (2017.01); *G06T 7/168* (2017.01); *G06T 7/174* (2017.01); *G06T 7/38* (2017.01); *G06T 2207/10088* (2013.01); *G06T 2207/20221* (2013.01); *G06T 2207/30016* (2013.01); *G06T 2207/30096* (2013.01); *G06T 2207/30101* (2013.01)

(58) Field of Classification Search
  USPC .... 382/274, 276, 286–291, 305, 312; 600/3; 378/4, 21
  See application file for complete search history.

(56) References Cited

U.S. PATENT DOCUMENTS

| | | | |
|---|---|---|---|
| 2009/0234175 | A1* | 9/2009 | Maier ................... A61N 5/1031 600/3 |
| 2013/0208961 | A1* | 8/2013 | Nieminen ................. G06T 7/11 382/128 |
| 2017/0021195 | A1* | 1/2017 | Schweizer ........... A61N 5/1039 |
| 2017/0103287 | A1* | 4/2017 | Han .......................... G06T 5/00 |

FOREIGN PATENT DOCUMENTS

| | | |
|---|---|---|
| CN | 105816192 A | 8/2016 |
| TW | I478697 B | 4/2015 |
| TW | 201603781 A | 2/2016 |
| TW | 201625182 A | 7/2016 |
| TW | 201719470 A | 6/2017 |
| WO | 2014171007 A1 | 10/2014 |
| WO | 2016007518 A1 | 1/2016 |

* cited by examiner

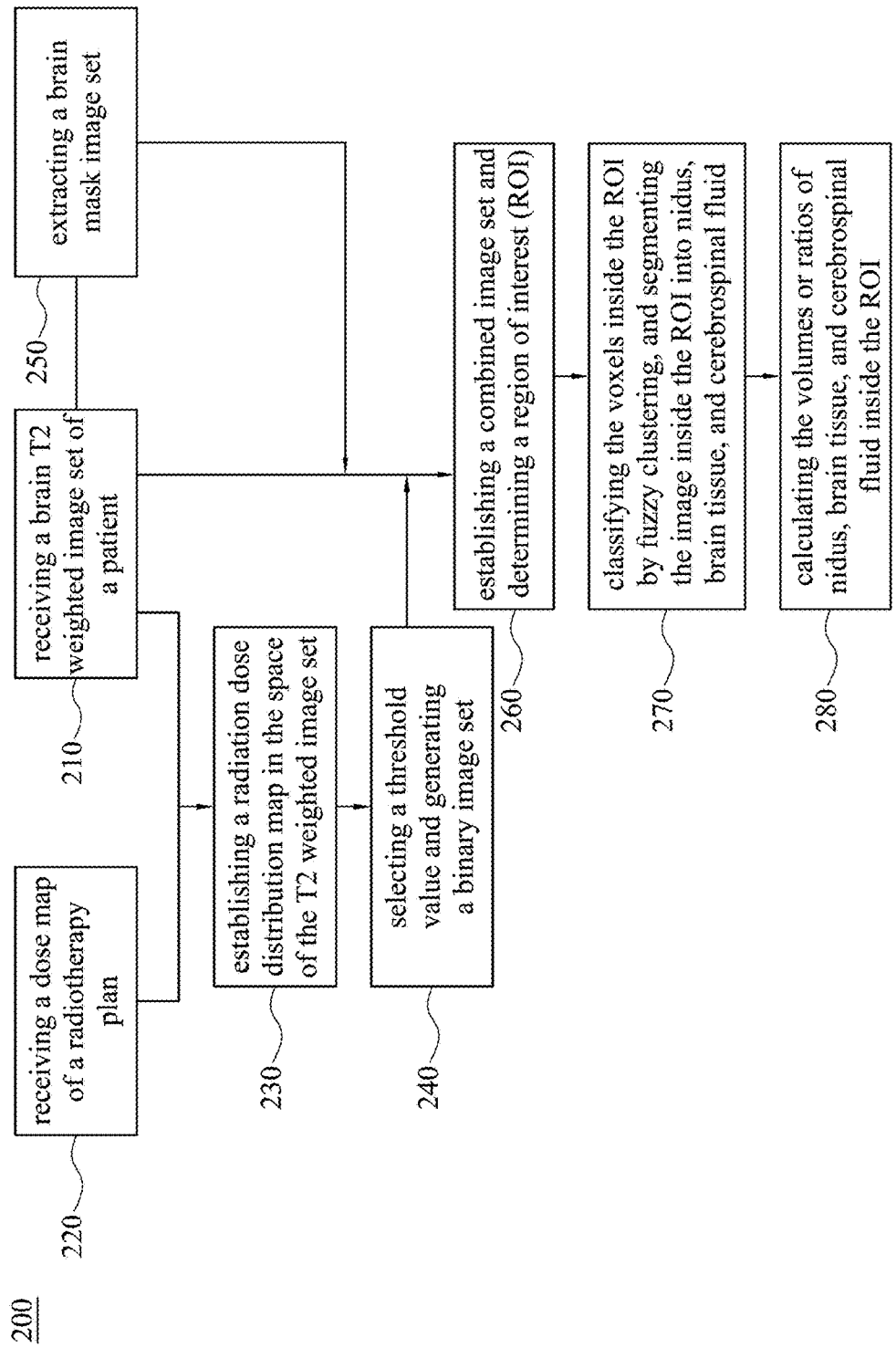

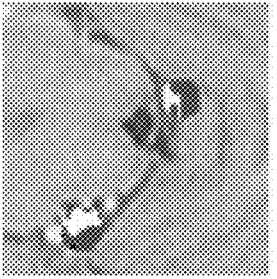
Fig. 12I
Fig. 12F
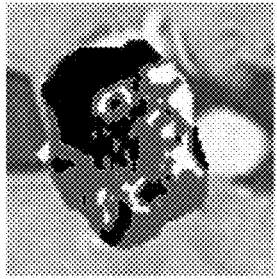
Fig. 12C
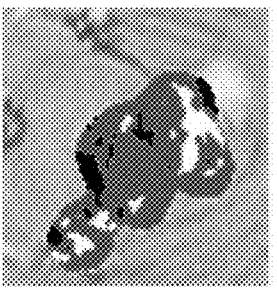
Fig. 12H
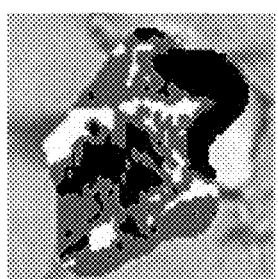
Fig. 12E
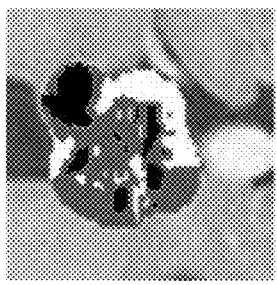
Fig. 12B
Fig. 12G
Fig. 12D
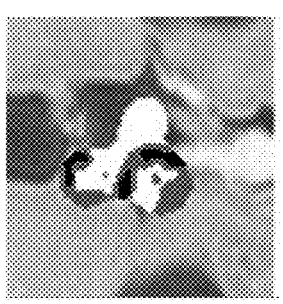
Fig. 12A

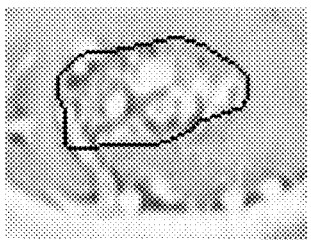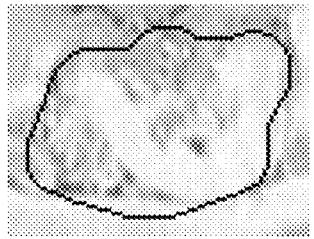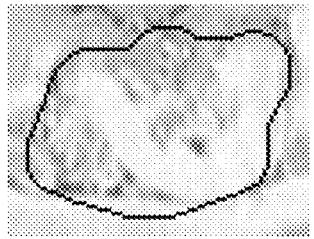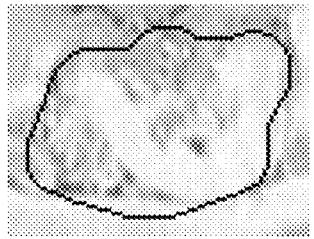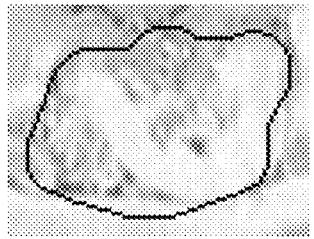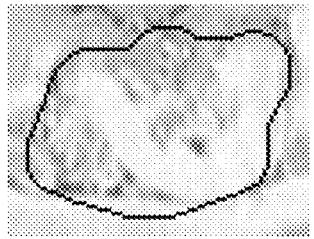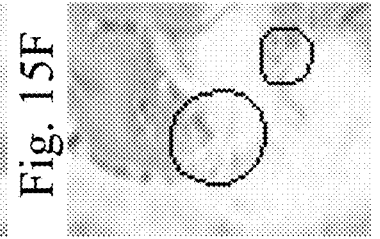

US 10,346,719 B2

MAGNETIC RESONANCE IMAGE ANALYSIS METHOD AND METHOD FOR EVALUATING THE RISKS OF RADIOTHERAPY

CROSS-REFERENCE TO RELATED APPLICATION

This application claims priority to Taiwan Application Serial Number 106132128, filed Sep. 19, 2017, which is herein incorporated by reference.

BACKGROUND

Field of Invention

The present disclosure relates to an analytical method for magnetic resonance image. More particularly, the present invention relates to an analytical method for analyzing the magnetic resonance image of patients receiving radiotherapy.

Description of Related Art

Magnetic Resonance (MR) Imaging has become an important tool in medical diagnosis in recent years. By this technique, human body profiles can be acquired without invasion of human bodies. It is important that MR image provides the structures of any cross section of soft tissues and many physical parameters. Moreover, MR imaging is free of ionizing radiation and radiation-related hazard.

Stereotactic radiosurgery achieves therapy effects by using imaging techniques, such as computed tomography (CT) and MR imaging, to locate the radiation rays precisely within the treated target and avoid damaging of the normal tissues surrounding the target. For example, for treating the lesion in brains, stereotactic radiosurgery can not only avoid the bleeding and infection risk, but also reduce the neuron damage caused by traditional craniotomy surgery. Stereotactic radiosurgery leads to no surgical scars, less bleeding, and quick recovery; therefore, patients can sooner return to their daily life or work. Hence, in recent years, stereotactic radiosurgery has become one of the major treatment options to various kinds of diseases, particularly in the neurosurgical lesions such like brain tumors or cerebral vascular lesions.

Although stereotactic radiosurgery is safer according to literature, complications occur in a few patients after radiotherapy, such as radiation necrosis, cerebral edema, or other neurological deficits related to radiation, etc. For example, it is well-known that a few patients suffer permanently from chronic expanded hematoma or post-radiation cyst, which causes mass effects several years after radiosurgery for arteriovenous malformations (AVMs). In rare cases, the complications may even cause death. Currently, the mechanisms of these long-term complications after radiosurgery are controversial; one of the hypotheses is radiation exposure of the normal brain tissue intervening the nidus during radiosurgery. However, there is a lack of good tools for analyzing the different types of tissues inside the target underwent radiotherapy.

Therefore, the present disclosure provides a method enable to analyze the different tissues inside the target underwent radiotherapy.

SUMMARY

One of the objects disclosed herein is to analyze the various types of tissues inside a radiation target by using MR images.

In view of the purpose, the present disclosure provides a method via assessing MR image of patients who prepared to receive radiotherapy; the method includes: receiving an MR image set and a radiotherapy plan of a patient; converting the dose intensity distribution positions of the dose map of the radiotherapy plan into the corresponding spatial positions in the MR image set; selecting a radiation dose and a radiation exposure region, wherein the radiation exposure region has radiation intensity being equal to or higher than the radiation dose; determining a region of interest (ROI) of the MR image set; classifying voxels inside the ROI of the MR image set into different clusters in accordance with the grayscale values of the voxels inside the ROI; and counting the volumes or ratios of the clusters inside the ROI.

The present disclosure also provides a method for evaluating risks of radiotherapy, including the following steps: acquiring the volumes or ratios of different clusters in a radiation exposure regions of an MR image set of patients; tracking symptoms after the radiotherapy of the patients; and establishing the correlation between the volumes or ratios of different clusters inside the radiation exposure regions of the MR image set and the symptoms after the radiotherapy of the patients.

By the present disclosure, the types of tissues inside the radiation exposure region can be analyzed and quantified.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiments, with reference made to the accompanying drawings as follows:

FIG. 3 is a flowchart of the operation procedure for image analysis according to some embodiments.

FIG. 12A through FIG. 12I are the respective results of automatic image segmentation for the images of different cross sections of FIG. 11A through FIG. 11I in accordance with one example.

FIG. 15A through FIG. 15I are MR images of different cross sections according to one example in accordance with one example.

DETAILED DESCRIPTION

Figure 1:
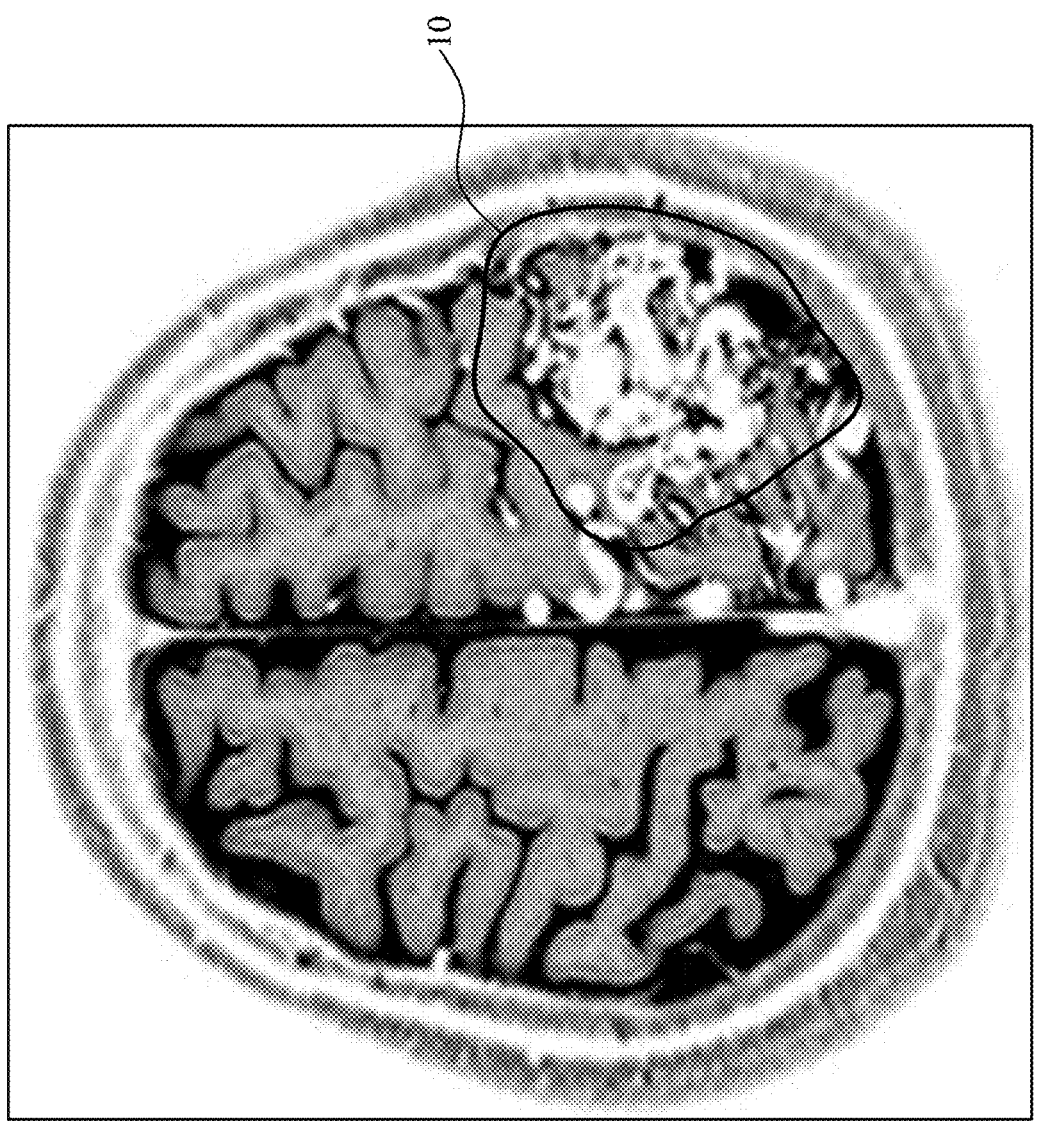
FIG. 1 is a brain MR T2 weighted image.

Reference will now be made in detail to the present embodiments of the invention, examples of which are illustrated in the accompanying drawings. Wherever possible, the same reference numbers are used in the drawings and the description to refer to the same or like parts.

In order to clearly display MR images, the gray scales in some of the MR images in the present disclosure are inverted, this converts darker portions into lighter portions, and lighter portions into darker portions in MR images.

In the disclosure, an MR image set include various MR images of different sections of an image taken region, and these images belong to a same image type and are taken in the same round of photographing.

In some embodiments, the radiation ray of the stereotactic radiosurgery is X ray, gammy ray, neutron beam, or proton beam. In some embodiments, stereotactic radiosurgery is X knife, Cyberknife, Gamma knife, Rapid-arc knife, Tomo-Therapy, Neutron Knife, or Proton knife.

In some examples, nidus which was treated with stereotactic radiosurgery includes: vascular diseases such as cerebral arterio-venous malformation (AVM), arteriovenous dural fistula, cavernous malformation, etc.; benign brain tumors such as vestibular schwannoma, meningioma, craniopharyngioma, pituitary adenoma, etc.; malignant brain tumors: such as metastatic brain tumor or glioma, etc. In addition, in some functional surgeries, such as the treatment for trigeminal neuralgia and the treatment for tremor symptoms of dyskinesia, the method of the present disclosure can also be applied to analyze the tissues inside the radiation exposure region.

Please refer to FIG. 1, which shows a brain MR T2 weighted image. For clarity of display, the grayscale of the image was inverted. Region 10 is a manually selected cerebral arterio-venous malformation (AVM). The voxels inside region 10 can be classified as different tissue types of the brain, according to the image intensity values (grayscale values). For example, in region 10, the white color part denotes to nidus, the gray color part denotes to brain tissue, and the black color part denotes to cerebrospinal fluid (CSF).

However, when the target is selected manually, the region under examination is not completely equal to the region in which is actually exposed to radiation during therapy. Therefore, the present disclosure provides a computer software-assisted identification method for selecting regions of interest (ROIs) of MR images. Hence, the ROIs are the irradiated targets when the patients receive radiotherapy.

In some embodiments of the present disclosure, the algorithm of the analyzing method is implemented by MATLAB program (The MathWorks, Inc., Natick, Mass., US).

Figure 2:
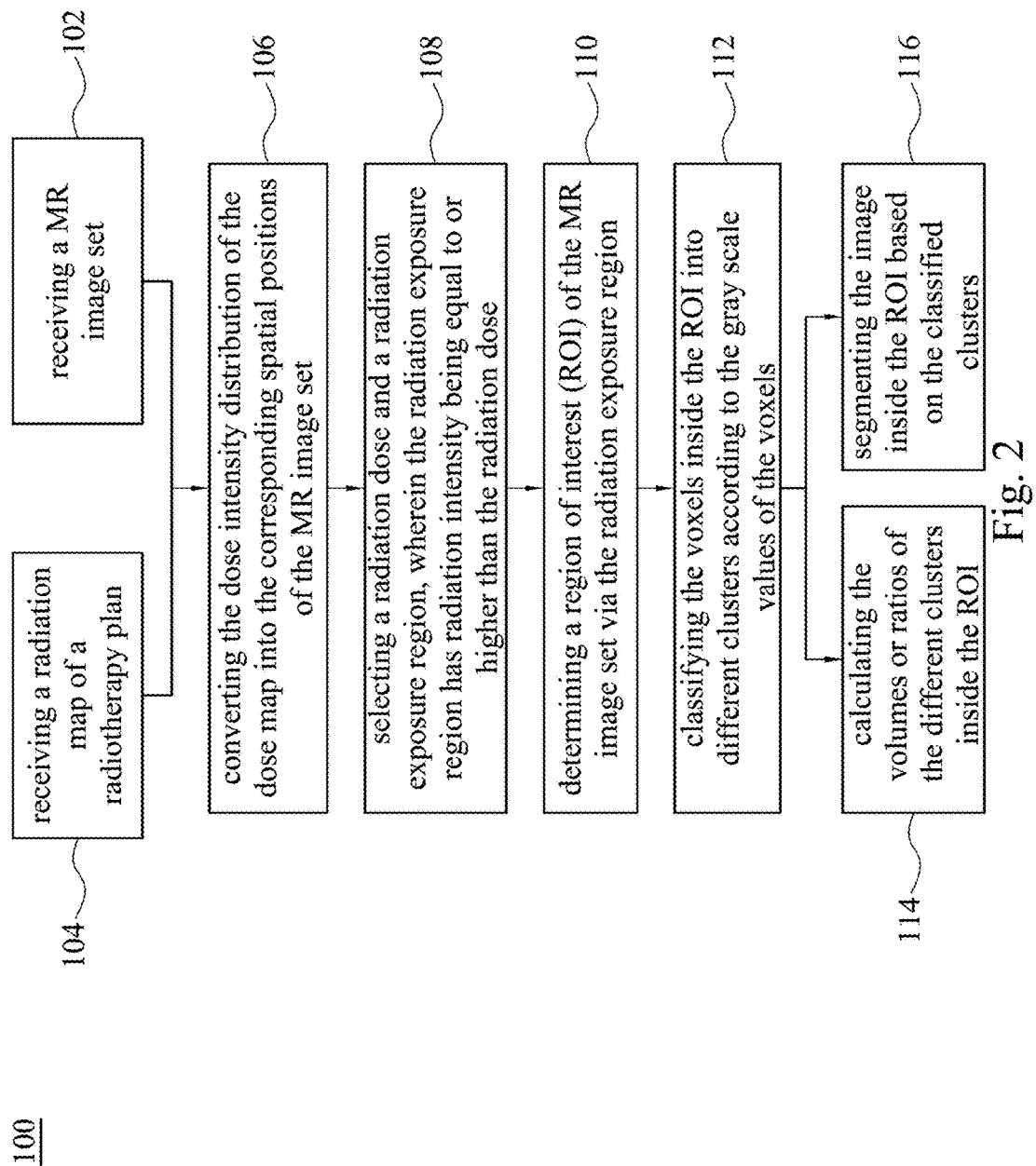
FIG. 2 is a flowchart of an image analysis method according to one embodiment of the present disclosure.

Please refer to FIG. 2, which is a flowchart of an image analysis method according to at least one embodiment of the present disclosure. Method 100 begins at step 102, receiving an MR image set, and step 104, receiving a dose map of a radiotherapy plan.

In at least one embodiment, the MR image set for analyzing may be the MR image set taken for positioning before radiotherapy or during the radiotherapy. The types of MR images may be, for example, T1 weighted image, T2 weighted image, diffusion weighted image, angiography, fractional anisotropy, apparent diffusion coefficient image, radial diffusivity and axial diffusivity image, blood oxygen level dependent image, T1 and T2 parameter-based image, T2 star (T2*) parameter-based image, or susceptibility parameter-based image.

Because different tissues express various levels of signal expression in different types of MR images, the different tissues display different levels of grayscale in MR images. For analysis, suitable types of MR images can be selected for displaying the better contrast between the interested tissues.

The dose map of radiotherapy plan is made according to the positioning photography before surgery and reconstruction of the three-dimensional image; then the best therapy plan was designed according to the location, size, or shape etc. of the target. The dose map includes parameters of the radiation dose intensity and the three-dimensional coordinate of the irradiated target.

Method 100 then proceeds to step 106, converting the dose intensity distribution positions of the dose map into the corresponding spatial positions of the MR image set.

In at least one embodiment, the MR image set and the radiotherapy plan have the same spatial coordinate system. For acquiring the dose of the corresponding special positions of the voxels of the MR image set, the dose intensity at each spatial coordinate in the dose map of the radiotherapy plan is imported to the corresponding spatial coordinates of the MR image set. Therefore, information of the radiation dose of the various voxels of the MR image set can be acquired. Consequently, this is beneficial for determining ROIs of the MR image set in voxels and in accordance with radiation dose intensity.

According to at least one embodiment, step 106 further includes extracting the Tag of Header information of Digital Imaging and Communications in Medicine (DICOM) of the MR image set and the dose map of the radiotherapy plan, and extracting the Dose Grid Scaling of the dose map of the therapy plan. Then, the radiation doses at the various voxel positions in the MR image set are multiplied by the dose grid scaling of the dose map; thereby acquiring the dose intensity distribution spectra in centigrays (cGys) in the space of the MR image. The following illustrates the detailed operation process by the T2 weighted image set and the dose map of a radiotherapy plan of a patient.

The image position, the voxel pitch, the grid frame offset vector, the number of rows, and the number of columns of the header information of the DICOM of the dose map of the radiotherapy plan were extracted. The image position indicates the special coordinate of the first voxel in the upper left corner of the dose map; this coordinate is shown as ($x\_{dose}$, $y\_{dose}$, $z\_{dose}$). The voxel pitch represents the distance between the voxels in x- or y-direction of the dose map.

Then, the vector $x\_{dose}$, the vector $y\_{dose}$, and the vector $z\_{dose}$ of the dose map were respectively constructed as follows. The vector $x\_{dose}$ was constructed from [$x\_{dose}$-coordinate of the dose map] to [$x\_{dose}$-coordinate of the dose map+the number of rows of the dose map*the voxel pitch of the dose map in x-direction−1], the pitch is [the voxel pitch of the dose map in x-direction]. Thus, a vector $x\_{dose}$ of the dose map was constructed in millimeters. The vector $y\_{dose}$ was constructed from [$y\_{dose}$-coordinate of the dose map] to [$y\_{dose}$-coordinate of the dose map+the number of columns of the dose map*the voxel pitch of the dose map in y-direction−1], and the pitch is [the voxel pitch of the dose map in y-direction]. Thus, a vector $y\_{dose}$ of the dose map was constructed in millimeters. The vector $z\_{dose}$ was constructed by $z\_{dose}$-coordinate of the dose map plus the grid frame offset vector; then a vector $z\_{dose}$ of the dose map was constructed in millimeters.

Then, the region defined by the vector $x\_{dose}$, the vector $y\_{dose}$, and the vector $z\_{dose}$ was transformed into a matrix of $X\_{dose}$, $Y\_{dose}$, and $Z\_{dose}$, and a three-dimensional grid matrix of the radiation intensity distribution was constructed.

The image position, the voxel pitch, the grid frame offset vector, the number of rows, and the number of columns of the DICOM header information of the T2 weighted (T2w) image were extracted. The image position indicates the spatial coordinate of the first voxel in the upper left corner of the T2 weighted image; this coordinate is shown as ($x\_{T2}$, $z\_{T2}$). The voxel pitch represents the distance between the voxels in x- or y-direction of the T2 weighted image.

Then, the vector $x\_{T2}$, the vector $y\_{T2}$, and the vector $z\_{T2}$ of the space of the T2 weighted image were respectively constructed as follows. The vector $x\_{T2}$ was constructed from [$x\_{T2}$-coordinate of the T2w image] to [$x\_{T2}$-coordinate of the T2w image+the number of rows of the T2w image*the voxel pitch of the T2w image in x-direction−1], and the pitch is [the voxel pitch of the T2w image in x direction]; Thus, a vector $x\_{dose}$ of the T2w image was constructed in millimeters. The vector $y\_{T2}$ was constructed from [$y\_{T2}$-coordinate of the T2w image] to [$y\_{T2}$-coordinate of the T2w image+the number of columns*the voxel pitch of the T2w image in y-direction−1], and the pitch is [the voxel pitch of the T2w image in y direction]; Thus, a vector $y\_{dose}$ of the T2w image was constructed in millimeters. The vector $z\_{T2}$ was constructed by $z\_{T2}$-coordinate of the T2w image plus the grid frame offset vector; then a vector $z\_{T2}$ of the T2w image was constructed in millimeters.

Then, the region defined by the vector $x\_{T2}$, the vector $y\_{T2}$, and the vector $z\_{T2}$ was transformed into a three-dimensional grid matrix of $x\_{T2}$, and $z\_{T2}$.

After the three-dimensional grid matrix of $X\_{dose}$, $Y\_{dose}$, and $Z\_{dose}$ and the three-dimensional grid matrix of $X\_{T2}$, $Y\_{T2}$, and $Z\_{T2}$ were constructed, the dose intensity distribution spectra of the three-dimensional grid matrix of $X\_{T2}$, $Y\_{T2}$, and $Z\_{T2}$ in the space of the T2w image set was generated by linear interpolation.

Referring still to FIG. 2, method 100 proceeds to step 108, selecting a radiation dose (unit: cGy) and a radiation exposure region, wherein the radiation exposure region has radiation intensity being equal to or higher than the radiation dose. In some embodiments, the intensity of the radiation dose is about 30, 50, 70, 90, 100, 110, 130, 150% intensity of the radiotherapy plan.

In at least one embodiment, the radiation dose intensity distribution in the space of the MR image set can be acquired via step 106; therefore, an amount of dose intensity can be selected, and then a region surrounded by the isodose curve of the dose intensity can be displayed. This region is the radiation irradiated target when the patient receives radiotherapy.

Then, the method 100 proceeds to step 110, determining a region of interest (ROI) of the MR image set via the radiation exposure region.

In at least one embodiment, the diagram of the dose distribution of the space of the MR image set can be combined with the MR image set. Then, a region corresponding to the radiation exposure region in the dose map is an ROI in the MR image set.

In at least one embodiment, a mask image set can be optionally used so that the ROI is also within the range of the mask defined in the mask image set. Because in some patients receiving radiotherapy, the regions surrounded by isodose curves may cover areas that are not suitable for examination. For example, in brain MR image, if the target locates near the skull, the region surrounded by an isodose curve will cover the skull and the area beyond the skull. Therefore, a mask image set can be used in this case. After the mask image set is combined with the MR image set, the ROI is determined to be within the space corresponding to the region of the mask; therefore, the target outside the mask region is excluded.

In at least one embodiment, the mask image set may be extracted by using the same MR image set, or by using another MR image set taken during position photography or taken during treatment. This another MR image set needs to be registered to the MR image set for analyzing. The procedure of registration is using the MR image set for analyzing as a reference, then adjusting this MR image set and another MR image set to make the voxels of the two MR image sets have a position correspondence relationship. In some examples, the image types of another MR image set may be Magnetic Resonance Angiography (MRA) of the patient. The MRA may be Time of flight (TOF) image, or Phase-Contrast (PC) image.

Referring still to FIG. 2, method 100 proceeds to step 112, classifying the voxels inside the ROI into different clusters according to the grayscale values of the voxels. The different clusters include the normal tissue or the diseased tissue within the organ of the target site of radiotherapy.

In some embodiments, the voxels inside the ROI are classified according to different algorithms. For example, the various voxels are classified by setting the thresholds of grayscale values of the different tissues, or by using fuzzy clustering. Fuzzy clustering is an unsupervised clustering technique. The principle of fuzzy clustering is dividing the data points into several clusters according to the distribution characteristics of the data points, and then focusing the data points in the different clusters to analyze.

In at least one embodiment, classification is carried out by using fuzzy C-means clustering. The principle of fuzzy C-means is adding fuzzy concept for classification, each data point is allowed to belong to different clusters, but the membership grades for the different clusters are different. In other words, each data point would not absolutely belong to any clusters, but rather each data point would be represented as a number between 0 and 1 to indicate the degree of the data point belonging to each cluster. Then, the membership grades of each data point for different clusters in the membership grade matrix can be examined, and the cluster with the largest value can be selected to serve as the cluster which the data point belongs to.

In some embodiments, the voxels of the ROI of a brain T2 weighted image set are classified by fuzzy C-means clustering. Moreover, the voxels are classified into three clusters, such as nidus, brain tissue, and cerebrospinal fluid, according to the difference in grayscale values of voxel between nidus, brain tissue, and cerebrospinal fluid in T2 weighted images. The detailed approach is shown below, wherein the information is expressed in numbers of 0-1 to indicate the degree to which each voxel belongs to each cluster. The expected number of clusters is N, and N equals to 3 (nidus, brain tissue, and cerebrospinal fluid). There are D voxel number in the radiation exposure region of the T2 weighted image ($x_1, x_2, \ldots x_D$). Each voxel has its own grayscale value. A N×D matrix U represents the degree of each voxel belonging to each of the cluster (membership grade). For example, for a data point $x_i$ in a brain T2 weighted image set, the sum of the membership grades belonging to the respective clusters equals to 1.

The function for fuzzy clustering is as follows:

$$\sum_{j=1}^{N=3} u_{ij} = 1, i = 1, 2, \ldots, D$$

Define the objective function according to the matrix U:

$$J_m = \sum_{i=1}^{D} \sum_{j=1}^{N=3} \mu_{ij}^m \|x_i - c_j\|^2$$

m is the fuzzy partition matrix exponent that controls the degree of fuzzy overlapping.

$c_j$ is the center of the jth cluster.

$u_{ij}$ is the degree of membership of data point $x_i$ in the jth cluster.

Then fuzzy clustering is carried out by the following steps.

Step 1: the cluster $u_{ij}$ is randomly initialized.

Step 2: the centers of various cluster (nidus, brain tissue, and cerebrospinal fluid) are calculated.

$$c_j = \frac{\sum_{i=1}^{D} \mu_{ij}^m x_i}{\sum_{i=1}^{D} \mu_{ij}^m}$$

Step 3: $u_{ij}$ is renewed according to the following formula.

$$u_{ij} = \frac{1}{\sum_{k=1}^{N=3} \left(\frac{\|x_i - c_j\|}{\|x_i - c_k\|}\right)^{\frac{2}{m-1}}}$$

Step 4: the objective function $J_m$ is calculated.

Step 5: steps 2-4 are iterated until improvement $J_m$ is smaller than a specified threshold amount or until a specific maximum number of iterations. For example, minimum amount of improvement $J_m$ is 1e-5; maximum number of iterations is 100.

Please still refer to FIG. 2, method 100 proceeds to step 114, calculating the volumes or ratios of the different clusters inside the ROI. The volumes and relative ratios of the different clusters inside the ROI can be acquired by the numbers of the voxels assigned to the respective clusters. Consequently, the tissue types within the radiation exposure region can be quantified.

Referring still to FIG. 2, method 100 may optionally include step 116, segmenting the image inside the ROI based on the classified clusters. The voxels classified into the same cluster are assigned the same label, and then the voxels are displayed in the same grayscale or the same color. Therefore, the ROI is divided into a number of non-overlapping regions for showing the special distribution characteristics of the various clusters inside the ROI.

Figure 4B:
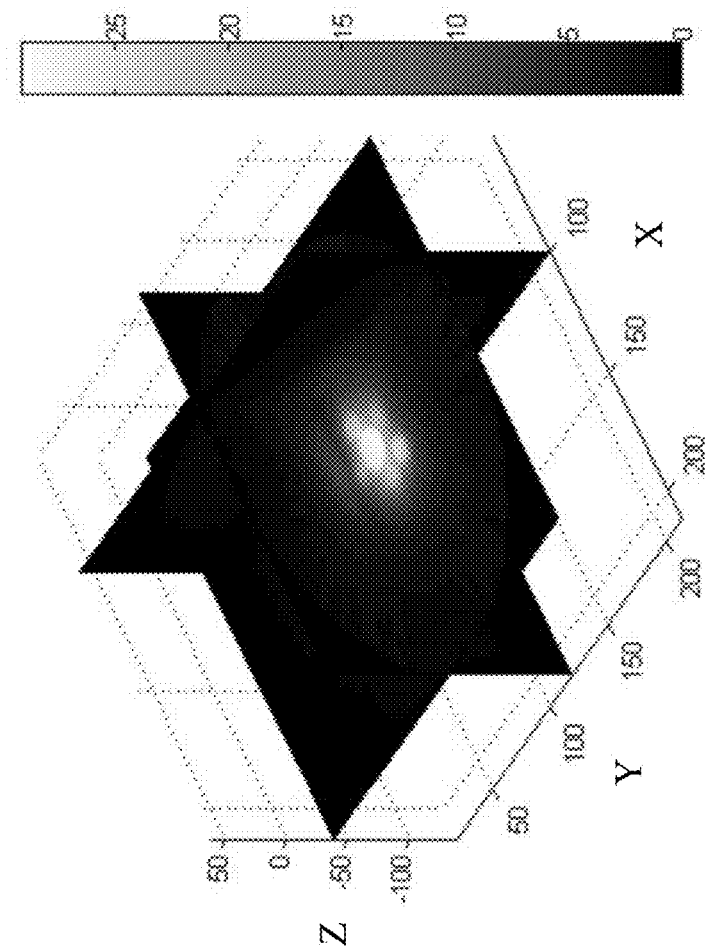
FIG. 4B is spectra of the dose intensity distribution of the radiotherapy plan according to one example.
Figure 4A:
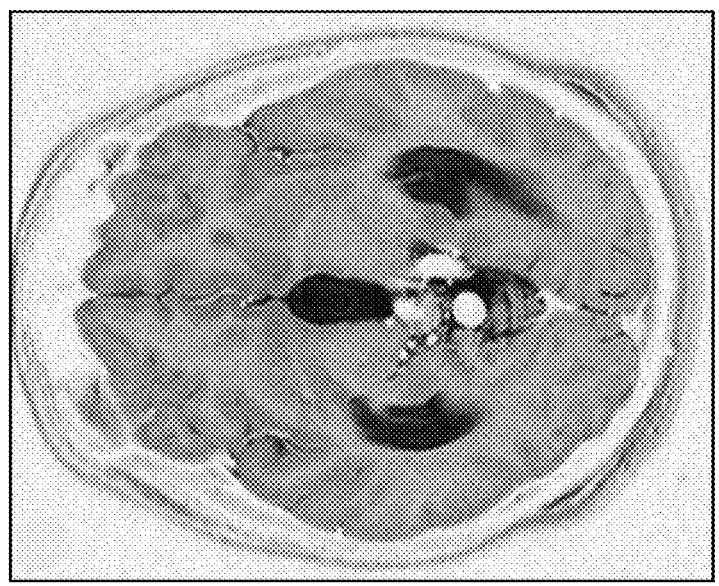
FIG. 4A is a brain MR T2 weighted image according to one example.

Please refer to FIG. 3, which shows an operational process for analyzing images of AVM patients receiving Gamma knife radiosurgery in accordance with some examples. Operation 200 begins at step 210, receiving a brain T2 weighted image set of a patient. Please refer to FIG. 4A, which is a brain T2 weighted image taken for positioning. Operation 200 includes step 220, receiving a dose map of a radiotherapy plan. Please refer to FIG. 4B; it shows the dose distribution spectra of the radiotherapy plan of a patient.

Figure 4D:
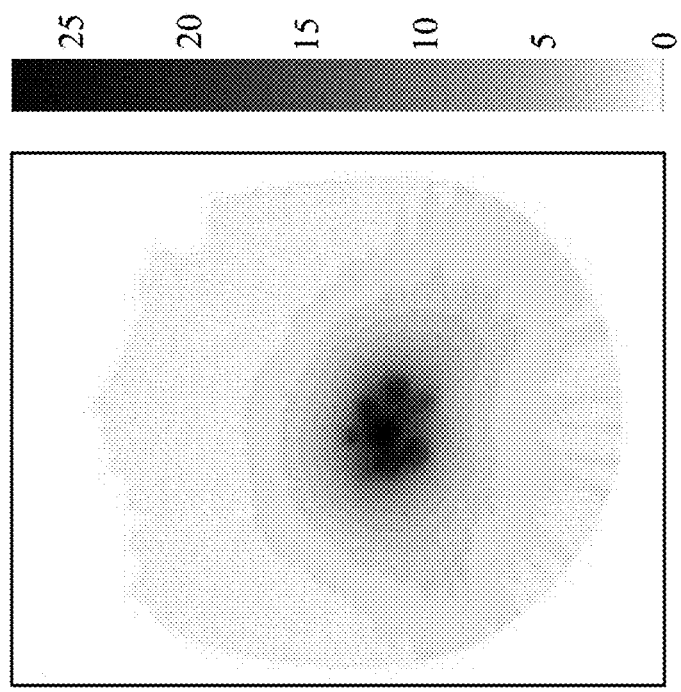
FIG. 4D is a diagram of the dose intensity distribution in the space of the brain MR T2 weighted image set.
Figure 4C:
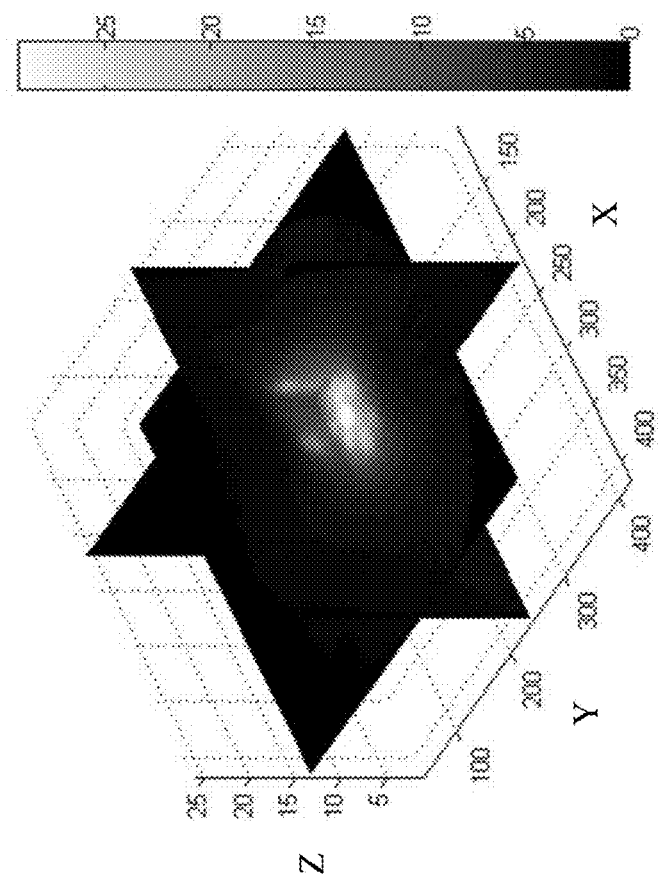
FIG. 4C is spectra of the dose intensity distribution in the space of brain MR T2 weighted image set according to one example.

Please refer to FIG. 3, operation 200 proceeds to step 230, establishing a radiation dose distribution map in the space of the T2 weighted image set. The radiation dose intensity distribution is transferred to the corresponding positions in the space of the T2 weighted image set by the step 106 of the method 100 described above. FIG. 4C shows radiation dose distribution spectra in the space of the brain T2 weighted image set of the patient. FIG. 4D is a cross-section image of FIG. 4C. FIG. 4D shows a diagram of the radiation dose intensity distribution in the space of the T2 weighted image set.

Figure 4F:
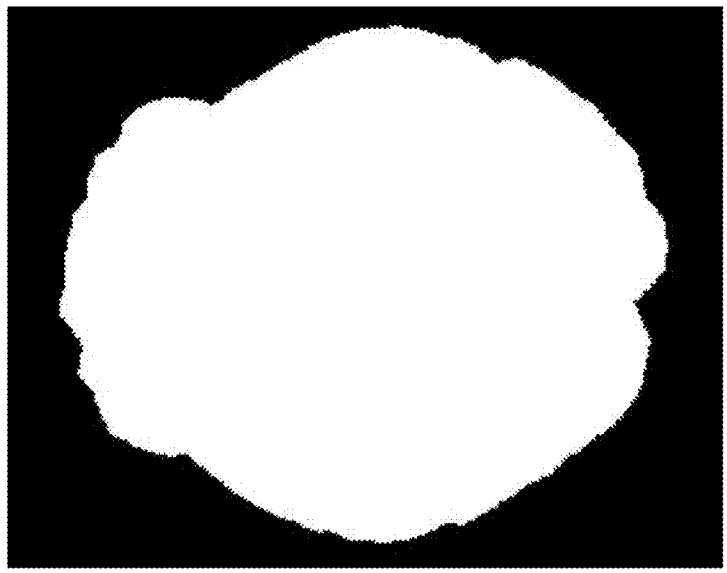
FIG. 4F is a brain mask image according to one example.
Figure 4E:
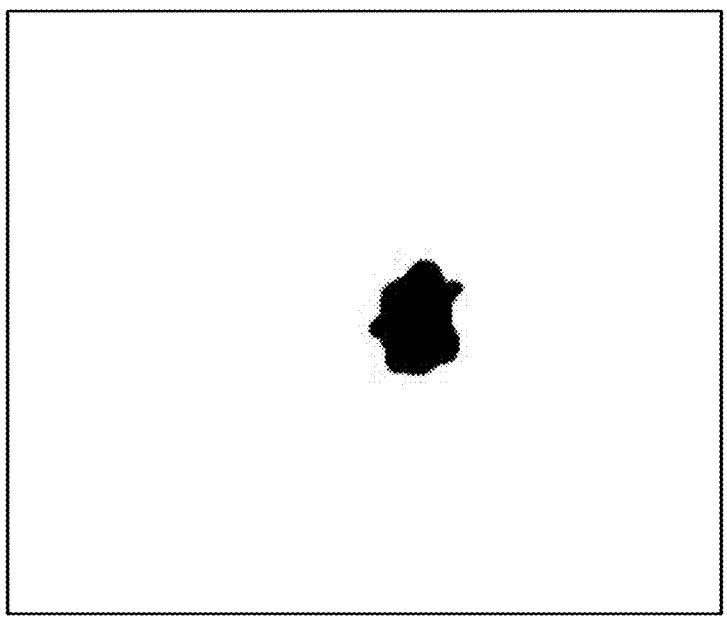
FIG. 4E is a binary image of the radiation dose intensity distribution according to one example.

Please refer to FIG. 3, operation 200 proceeds to step 240, selecting a threshold value and generating a binary image set. In this embodiment, 100% radiation dose intensity of the radiotherapy plan is selected to serve as a threshold. FIG. 4E shows a binary image of radiation dose distribution, in which the region with radiation equal to or greater than the threshold is shown in black, and other regions are shown in white.

Please refer to FIG. 3, operation 200 proceeds to step 250, extracting a brain mask set. Extracting brain mask set is carried out by using the brain T2 weighted image set of the patient. In some examples, a brain extraction toolbox of FMRIB Software Library (FSL) is used to remove the skull and the tissues not being inside the brain. As shown in FIG. 4F, the figure shows a brain mask image extracted from the brain T2 weighted image set of the patient.

Please refer to FIG. 3, operation 200 proceeds to step 260, establishing a combined image set and determining an ROI.

Figure 4H:
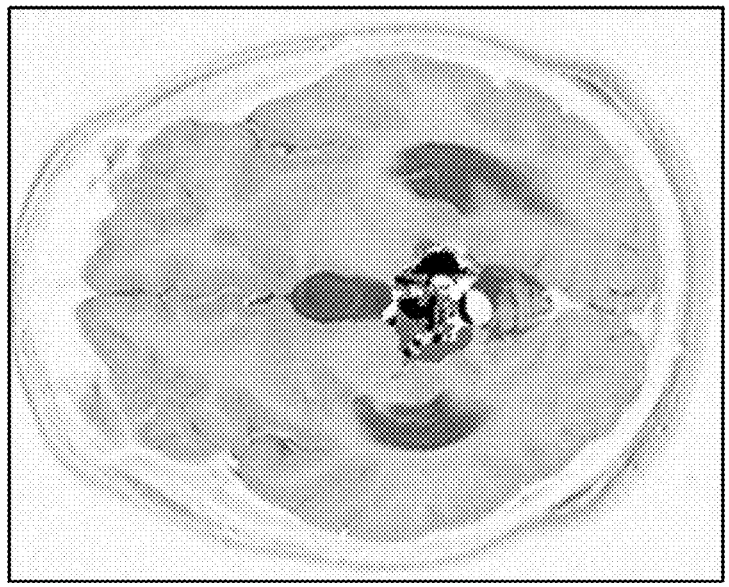
FIG. 4H is the result of image segmentation of an ROI of an MR image according to one example.
Figure 4G:
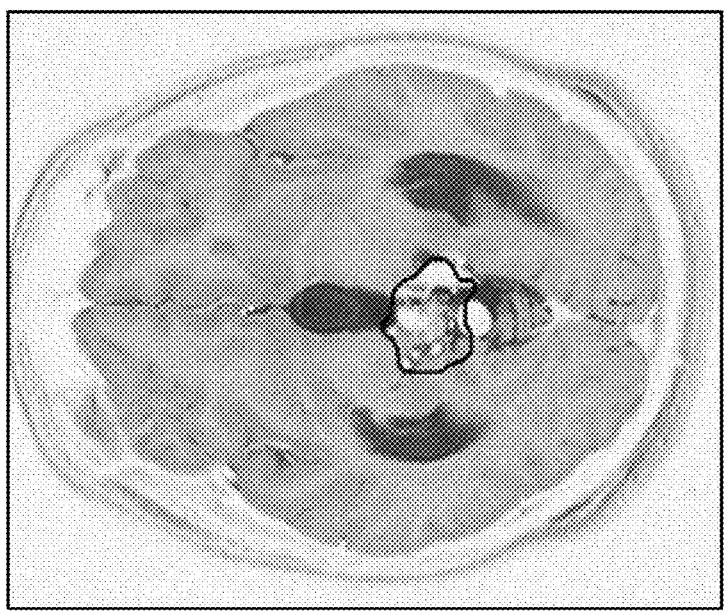
FIG. 4G shows a region of interest (ROI) of an MR image according to one example.

The brain T2 weighted image set, binary image set, and brain mask image set are combined to generate a combined image set. The ROI is within the brain mask and within the region corresponding to the black region of the binary image set. FIG. 4G shows a combined image of the patient, in this figure, the region surrounded by the black line is an ROI.

Please still refer to FIG. 3, operation 200 proceeds to step 270, classifying the voxels inside the ROI by fuzzy clustering, and segmenting the image inside the ROI into nidus, brain tissue, and cerebrospinal fluid. As shown in FIG. 4H, the region corresponding to the ROI of FIG. 4G is segmented into three different tissues: black denotes nidus, gray denotes brain tissue, and white denotes cerebrospinal fluid.

Please still refer to FIG. 3, operation 200 proceeds to step 280, calculating the volumes or the ratios of nidus, brain tissue, and cerebrospinal fluid inside the ROI.

Figure 5:
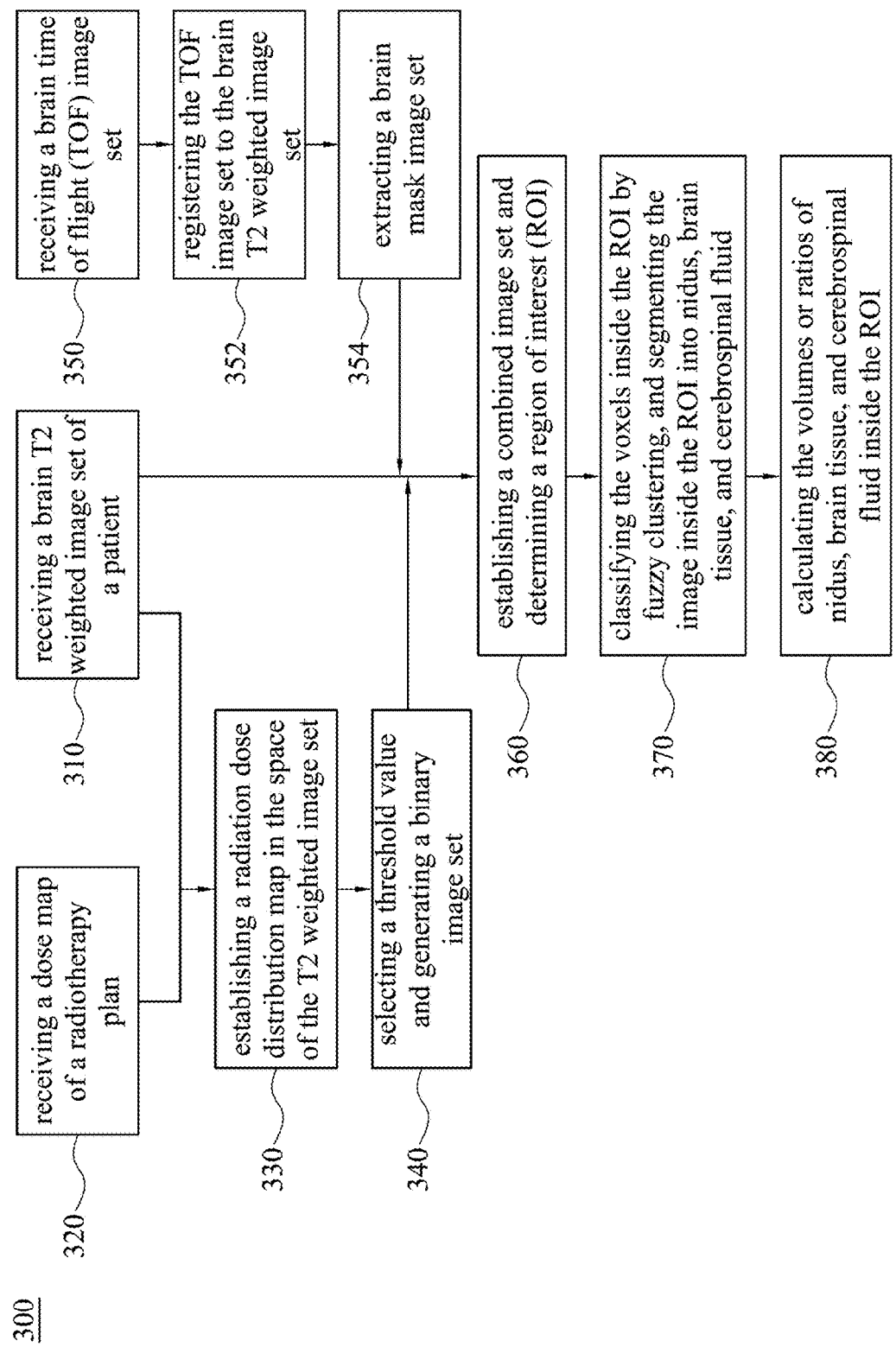
FIG. 5 is a flowchart of the operation procedure for image analysis according to some examples.

Referring to FIG. 5, it shows an operational process for analyzing images of an AVM patient receiving Gamma knife radiosurgery in accordance with some examples. Steps 310, 320, 330, 340, 360, 370, and 380 of operation 300 are similar to steps 210, 220, 230, 240, 260, 270, and 280 of operation 200.

Figure 6B:
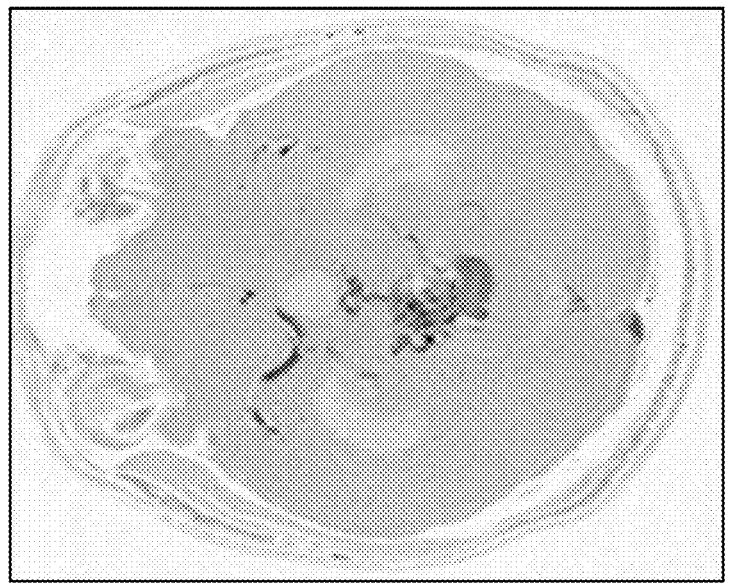
FIG. 6B is a time of flight image after image registration according to one example.
Figure 6A:
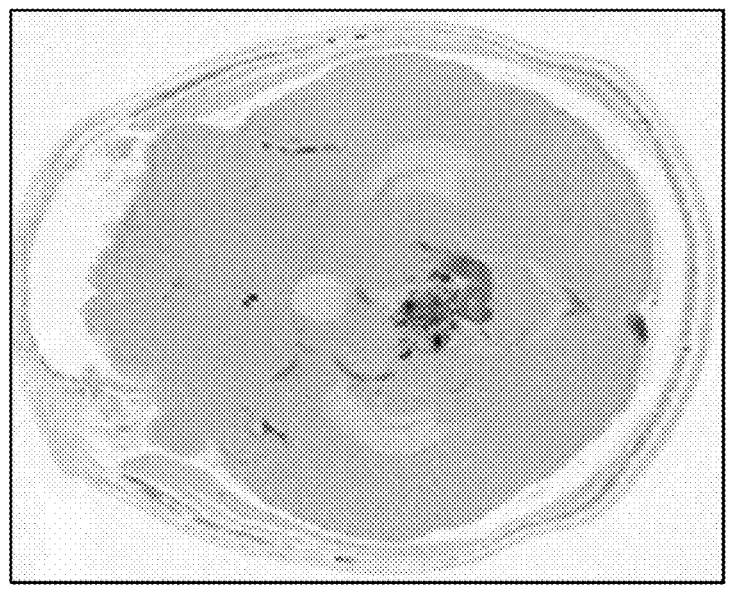
FIG. 6A shows a time of flight image according to one example.
Figure 6C:
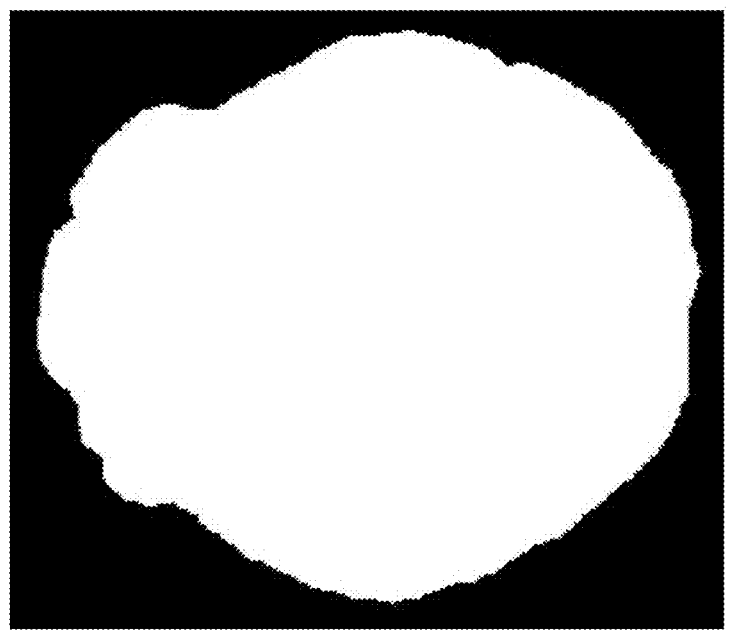
FIG. 6C shows an image of a brain mask according to one example.

Step 350 of operation 300 is receiving a brain time of flight (TOF) image set. FIG. 6A shows the TOF image of a patient. Then, step 352 is registering the TOF image set to the brain T2 weighted image set. FIG. 6B shows the registered TOF image. Then, step 354 is extracting a brain mask image set. FIG. 6C shows a brain mask image extracted from a registered TOF image set of a patient.

Figure 7B:
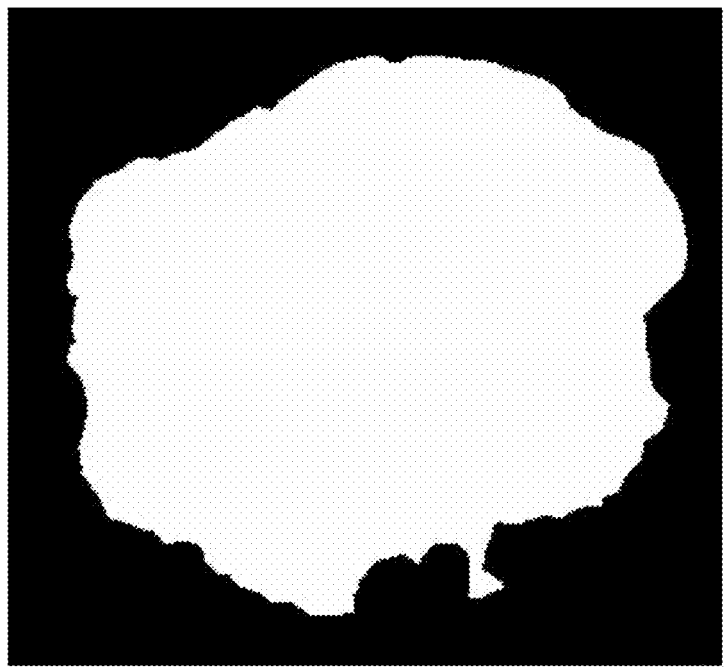
FIG. 7B is an image of a brain mask according to one example.
Figure 7A:
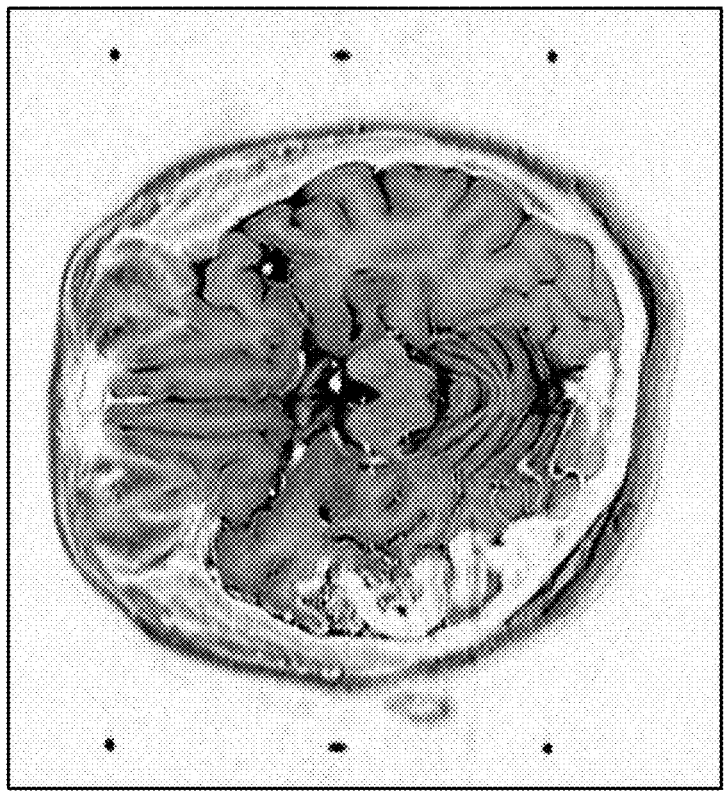
FIG. 7A is a brain MR T2 weighted image according to one example.

Operation 200 differs from operation 300 in that the image sources for extracting the mask image set are different. Because different image types have different contrast for different tissues, different types of MR images may be selected for extracting the mask images. For example, FIG. 7A shows a T2 weighted image of a patient, the left white part inside the skull is a target of cerebral AVM. FIG. 7B is a brain mask image extracted from FIG. 7A. FIG. 7B shows that brain region near the diseased vessels is not within the range of the extracted mask.

Figure 7D:
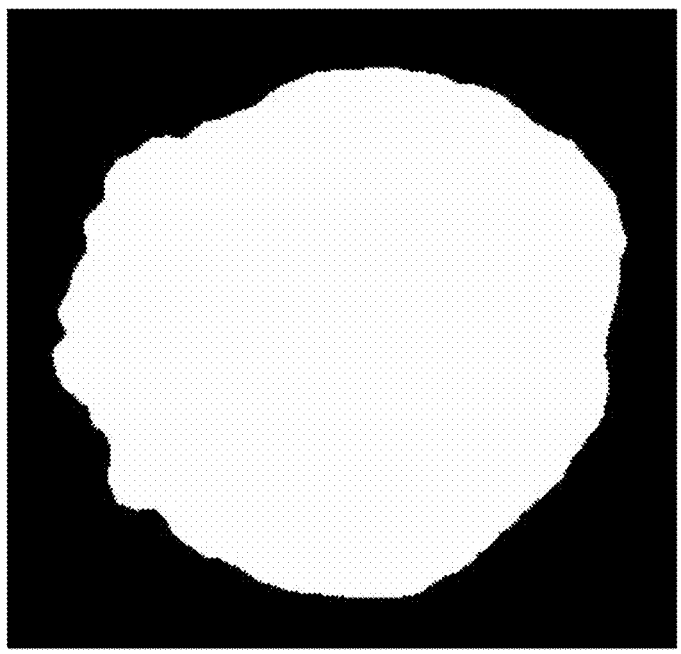
FIG. 7D is an image of a brain mask according to one example.
Figure 7C:
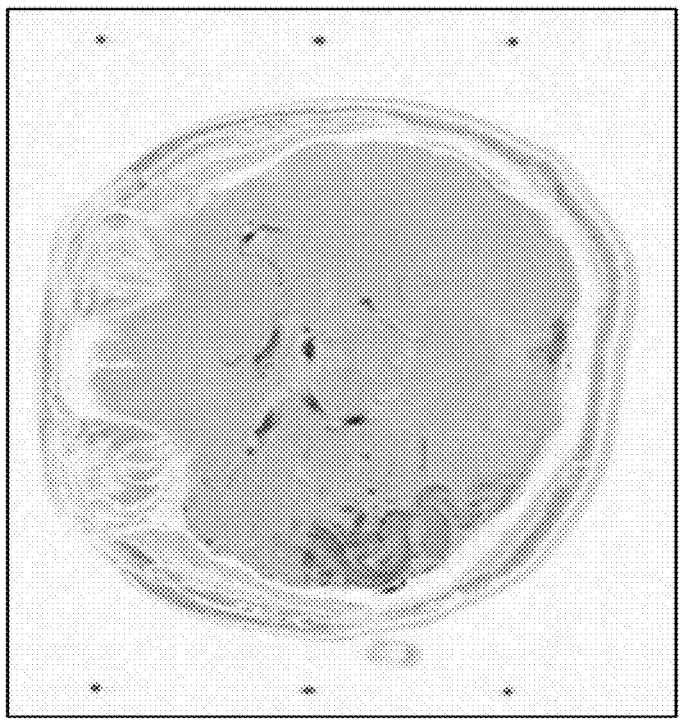
FIG. 7C is a time of flight image according to one example.

FIG. 7C is a TOF image of the same patient as in FIG. 7A, in which the diseased vessels are displayed in darker gray. FIG. 7D shows the brain mask image extracted from FIG. 7C. FIG. 7D shows the extracted mask covers the brain region near the diseased vessels. FIG. 7A and FIG. 7C are MR images of the same patient, but brain mask images extracted from the two figures have different ranges of the masks, as shown in FIG. 7B and FIG. 7D. Therefore, the mask image can be extracted by selecting an appropriate MR image type according to the location of the target.

Figure 8:
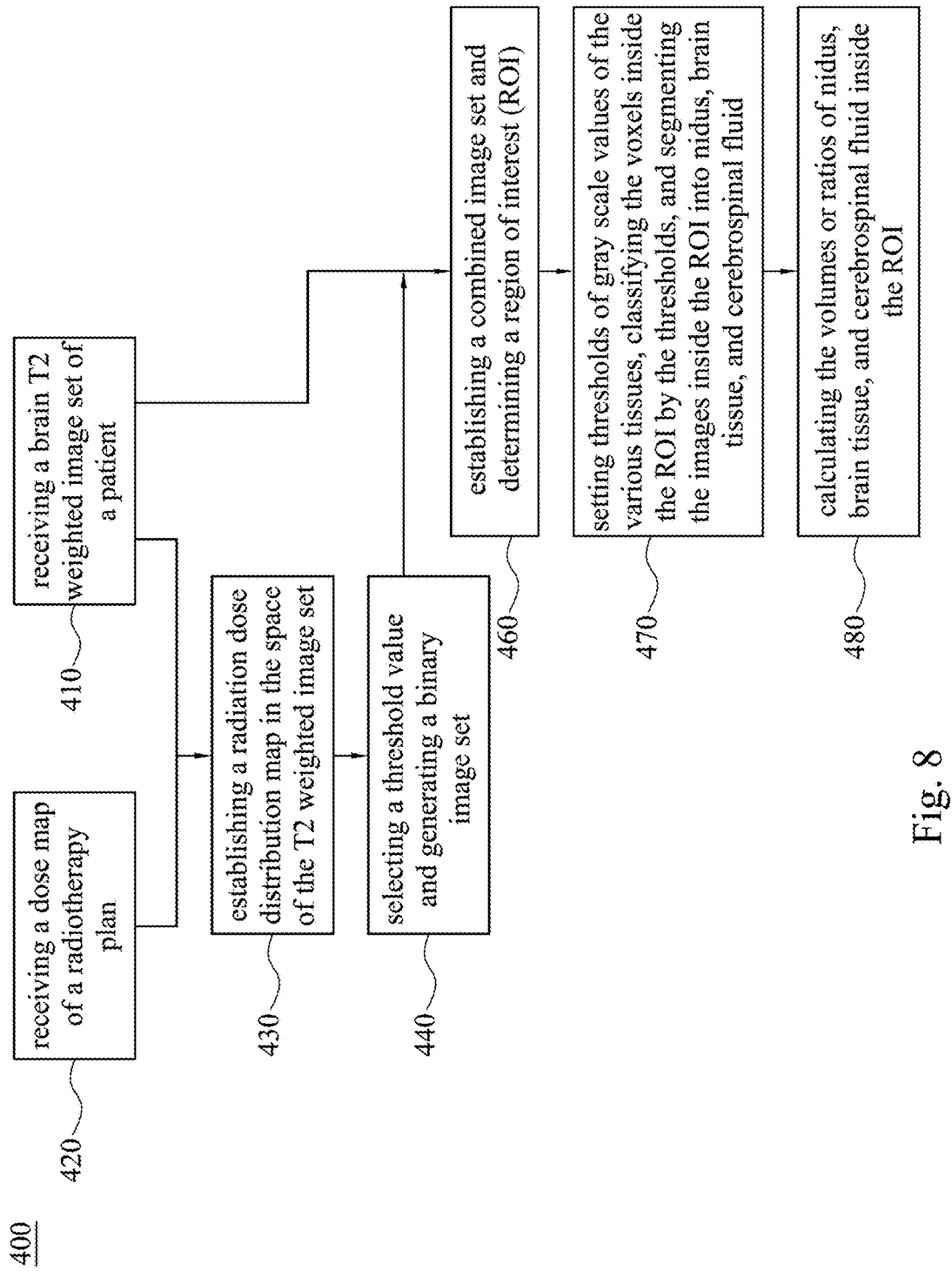
FIG. 8 is a flowchart of the operation procedure for image analysis according to some examples.
Figure 9B:
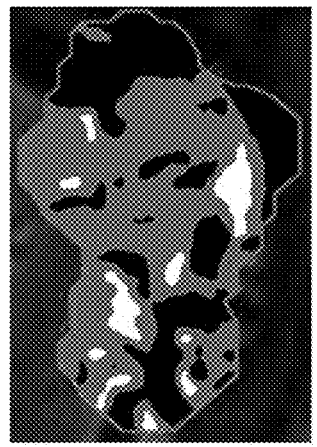
FIG. 9A through FIG. 9E show the results of image segmentation in the regions of interest (ROIs) according to one example.
Figure 9A:
Figure 9E:
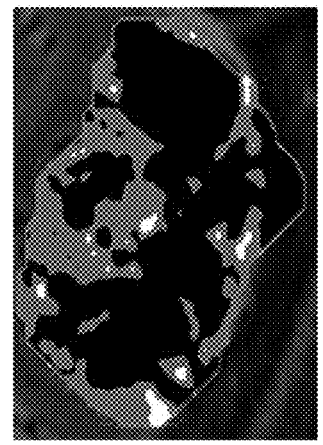
Figure 9D:
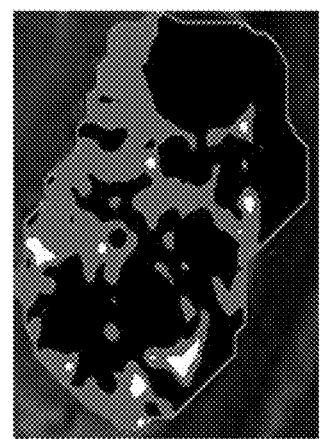
Figure 9C:
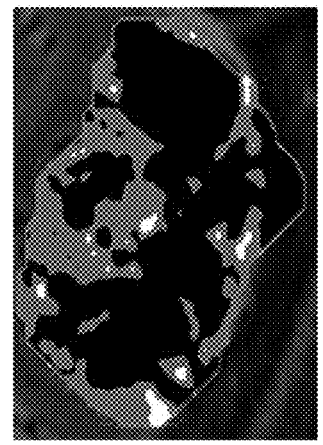

FIG. 8 shows an operation process for analyzing images of AVM patients receiving Gamma knife radiosurgery in accordance with some examples. Steps 410, 420, 430, 440, 460, and 480 of operation 400 are similar to steps 210, 220, 230, 240, 260, and 280 of operation 200. The operation 400 differs from the operation 200 in that a mask image set is not used in operation 400, and the classifying procedures of the two operations are different.

Operation 400 includes step 470, setting thresholds of grayscale values of the various tissues, classifying the voxels inside the ROI by the thresholds, and segmenting the images inside the ROI into nidus, brain tissue, and cerebrospinal fluid. For example, if the grayscale value of a voxel is smaller than 40, the voxel is classified as nidus; if the grayscale value of a voxel is greater than 40 but smaller than 80, the voxel is classified as brain tissue; if the grayscale value of a voxel is greater than 80, then the voxel is classified as cerebrospinal fluid. Therefore, the threshold of the grayscale for each tissue is nidus<brain tissue<cerebrospinal fluid. It is noted that in this embodiment, the numerical values of these thresholds may be determined depending on the images of different patients.

FIG. 9A through FIG. 9E are image segmentation results according to operation 400 in accordance with one example. FIG. 9A through FIG. 9E are various cross sections of a target. The regions surrounded by the gray lines are ROIs, in which black represents nidus, gray represents brain tissue, and white represents cerebrospinal fluid. The calculated results showed that in the ROI of the MR image set, the percentage of nidus is 51.5026%, the percentage of brain tissue is 45.7998, and the percentage of cerebrospinal fluid is 2.6795%.

In order to determine the accuracy and reliability of the automatic fuzzy clustering procedure of the present disclosure, the results of the experimental examples and the comparative examples of patients are provided below. In the experimental examples, image segmentation was carried out by computer software for automatic segmentation (automatic segmentation), and in the comparative examples, image segmentation was manually (manual segmentation) carried out by neurologists.

Figure 10A:
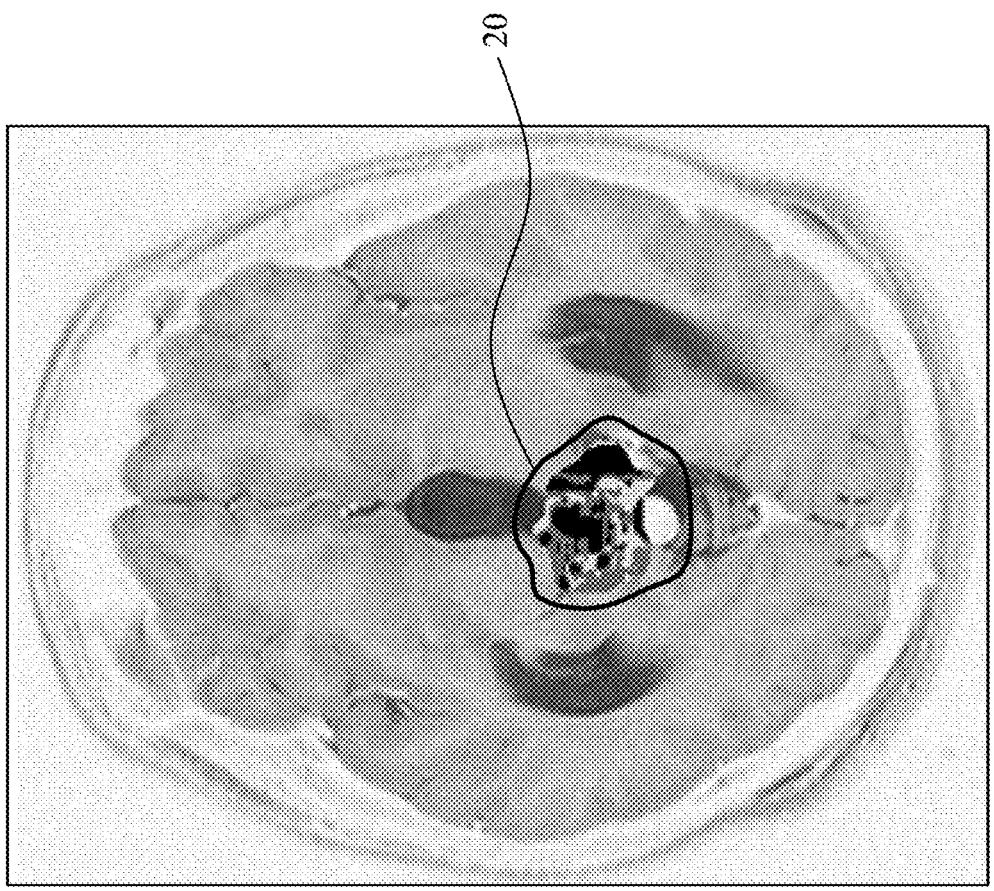
FIG. 10A shows the result of manual image segmentation according to one comparative example.
Figure 10B:
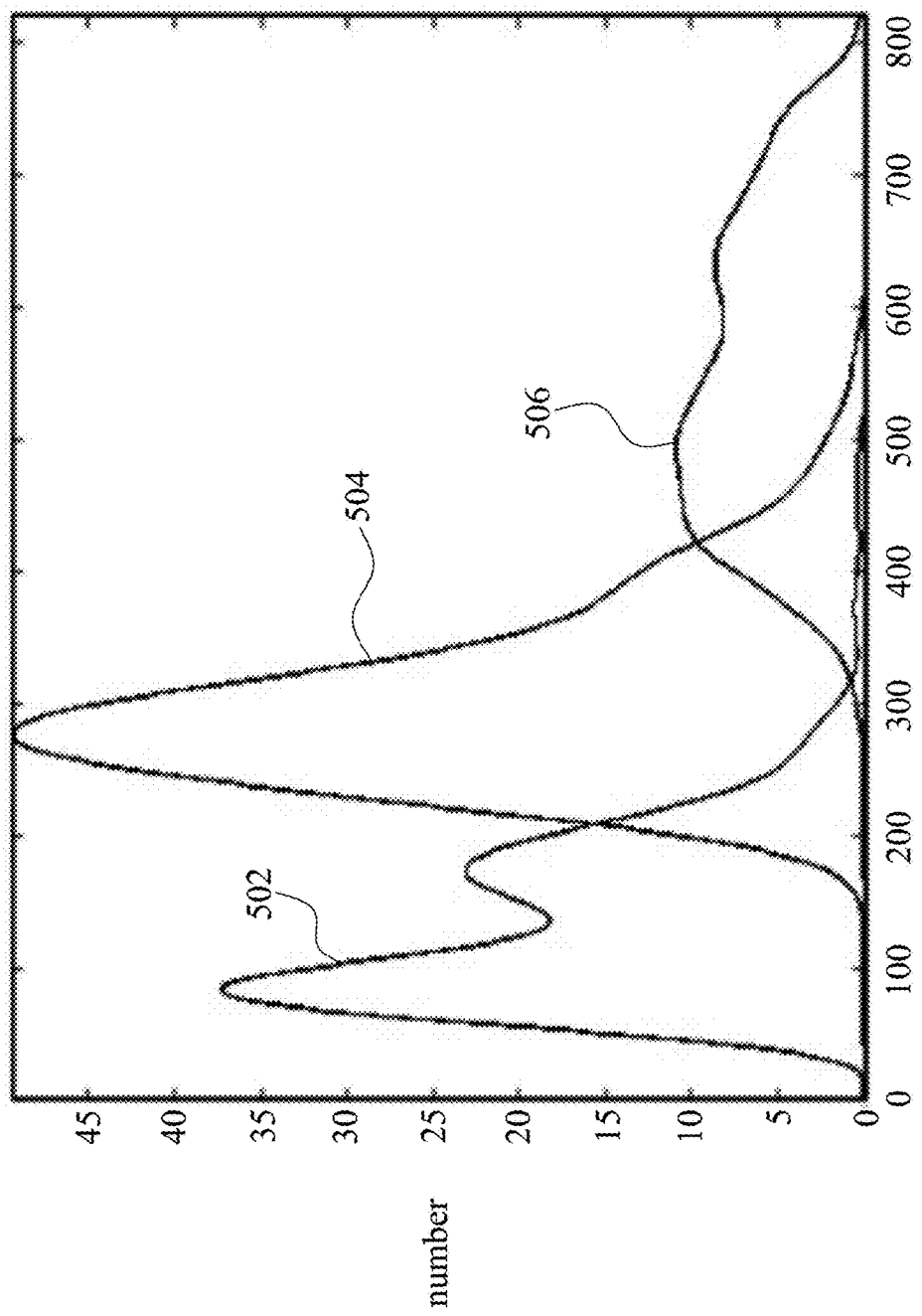
FIG. 10B shows the distribution of the grayscale values of the clusters in FIG. 10A.
Figure 11C:
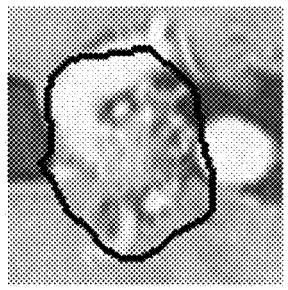
FIG. 11A through FIG. 11I are MR images of different cross sections according to one example.
Figure 11F:
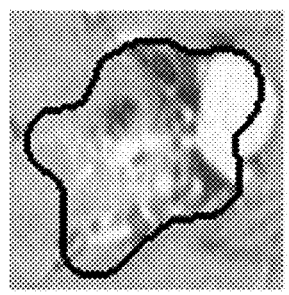
Figure 11I:
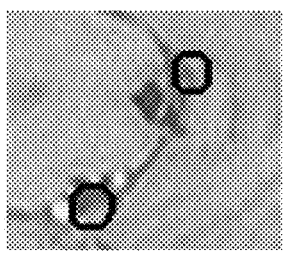
Figure 11B:
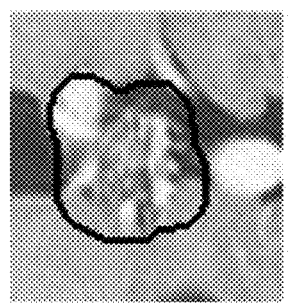
Figure 11E:
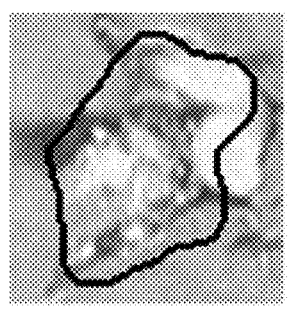
Figure 11H:
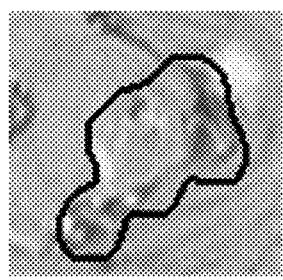
Figure 11A:
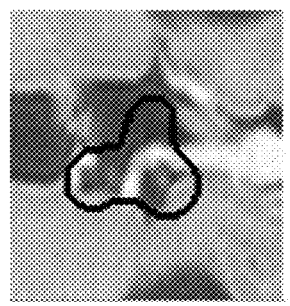
Figure 11D:
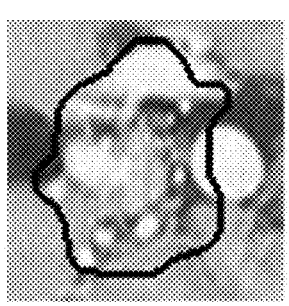
Figure 11G:
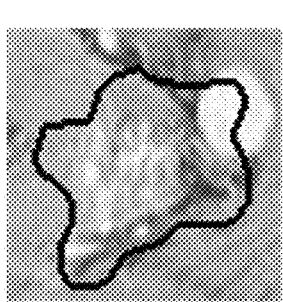
Figure 13C:
FIG. 13A through FIG. 13I are the respective results of the automatic image segmentation for the images of different cross sections of FIG. 11A through FIG. 11I in accordance with one comparative example.
Figure 13F:
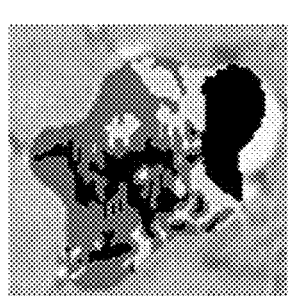
Figure 13I:
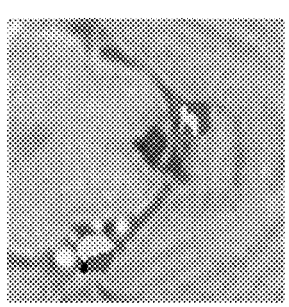
Figure 13B:
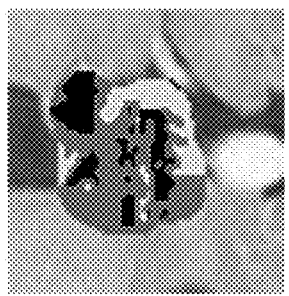
Figure 13E:
Figure 13H:
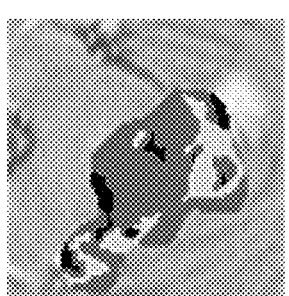
Figure 13A:
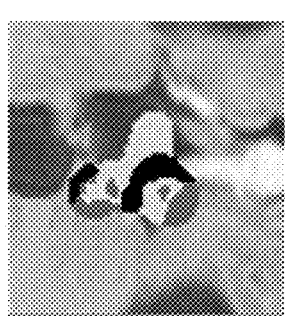
Figure 13D:
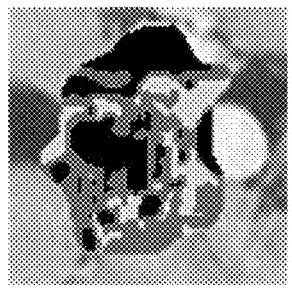
Figure 13G:
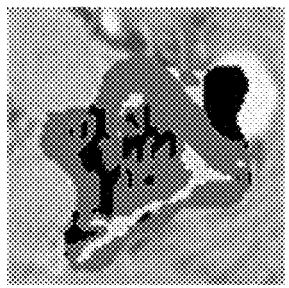

FIG. 10A is an image of a comparative example, in which area 20 includes a radiation exposure region, which was an ROI acquired by applying method 100 described above, and then the image inside ROI was examined, and the distributions of nidus, brain tissue and cerebrospinal fluid were manually delineated by a neurologist. In this figure, black represents nidus, gray represents brain tissue, and white represents cerebrospinal fluid. FIG. 10B shows the histogram of the various voxels of the three tissues in FIG. 10B classified by manual segmentation. Line 502 is the histogram of the voxel grayscales values of the nidus, line 504 is the histogram of the voxel grayscales values of the brain tissue, and line 506 is the histogram of the voxel grayscales values of the cerebrospinal fluid. FIG. 10B shows that the voxel grayscale values of these three tissue types are partially overlapped with one another.

In order to determine the accuracy of the automatic segmentation procedure of the present disclosure, the results from manual segmentation performed by a neurologist serve as standards (gold standards), and are compared with the results from the automatic segmentation of operation 200. Similarity Index (SI) is used for determining the degree of similarity between comparative examples and experimental examples. Moreover, sensitivity and specificity are also used for determining accuracy of the automatic segmentation.

Table 1 below shows the ratios of the three tissues of the brains within the ROI by using the automatic segmentation procedure. Table 1 shows the different ratios of the three tissues of ROIs of 5 patients. In particular, the lowest ratio of brain tissue is 37.13%, and the highest ration of brain tissue is 56.55. Therefore, different patients have different ratios of brain tissue exposed to radiation during radiotherapy.

TABLE 1

|  | nidus (%) | Brain tissue (%) | cerebrospinal fluid (%) |
|---|---|---|---|
| Patient A | 48.40 | 39.41 | 12.19 |
| Patient B | 29.48 | 50.89 | 19.63 |
| Patient C | 24.17 | 56.55 | 19.29 |
| Patient D | 48.70 | 37.13 | 14.16 |
| Patient E | 41.75 | 43.89 | 14.36 |

Table 2 shows the similarity index between the results of the automatic segmentation procedure and the manual segmentation procedure. Table 2 shows the results of the two procedures have a high degree of correlation. Among the results, the average values of SI of the nidus, the brain tissue, and the cerebrospinal fluid are 0.741±0.168%, 0.803±0.064%, and 0.802±0.095%, respectively. Therefore, the results of the automatic segmentation procedure and the manual segmentation procedure of these examples have high similarity.

TABLE 2

|  | Similarity Index | | |
| --- | --- | --- | --- |
|  | nidus | brain tissue | cerebrospinal fluid |
| patient A | 0.7504 | 0.8453 | 0.9174 |
| Patient B | 0.8313 | 0.8619 | 0.8932 |
| patient C | 0.4469 | 0.8248 | 0.7414 |
| Patient D | 0.8251 | 0.7037 | 0.7242 |
| Patient E | 0.8490 | 0.7790 | 0.7349 |
| Mean value | 0.741 | 0.803 | 0.802 |
| Standard deviation | 0.168 | 0.064 | 0.095 |

Table 3 shows the sensitivity and specificity between the results of automatic segmentation and manual segmentation. The average values of sensitivity for the nidus, the brain tissue, and the cerebrospinal fluid are 0.723±0.254%, 0.889±0.051% and 0.729±0.154%, respectively; the average values of specificity of the three tissue types are 0.966±0.021%, 0.728±0.146% and 0.956±0.017%, respectively. Therefore, the automatic segmentation procedure of present examples has a good correlation with the manual segmentation procedure.

TABLE 3

|  | sensitivity | | | specificity | | |
| --- | --- | --- | --- | --- | --- | --- |
|  | nidus | Brain tissue | cerebrospinal fluid | nidus | Brain tissue | cerebrospinal fluid |
| Patient A | 0.6387 | 0.9202 | 0.8865 | 0.9912 | 0.8382 | 0.9553 |
| Patient B | 0.8997 | 0.8267 | 0.9067 | 0.9354 | 0.9070 | 0.9470 |
| Patient C | 0.3141 | 0.9511 | 0.6496 | 0.9785 | 0.5364 | 0.9670 |
| Patient D | 0.8517 | 0.8508 | 0.6058 | 0.9654 | 0.6747 | 0.9340 |
| Patient E | 0.9118 | 0.8961 | 0.5987 | 0.9599 | 0.6843 | 0.9781 |
| Mean value | 0.723 | 0.889 | 0.729 | 0.966 | 0.728 | 0.956 |
| Standard deviation | 0.254 | 0.051 | 0.154 | 0.021 | 0.146 | 0.017 |

Please refer to FIG. 11A through FIG. 11I, FIG. 12A through FIG. 12I, and FIG. 13A through FIG. 13I. FIG. 11A through FIG. 11I are different cross sections of MR images of a patient, in which the regions surrounded by the black line are a target region received radiation radiotherapy, and the target regions are ROIs acquired by the processes of operation 200. FIG. 12A through FIG. 12I shows the distribution of three tissues acquired by the automatic segmentation procedure for the ROIs of FIG. 11A through FIG. 11I, respectively. FIG. 13A through FIG. 13I shows the distribution of three tissues acquired by the manual segmentation procedure for the ROIs of FIG. 11A through FIG. 11I, respectively. In the ROIs of FIG. 12A through FIG. 12I, and FIG. 13A through FIG. 13I, black color represents nidus, gray color represents brain tissue, and white color represents cerebrospinal fluid.

Respective comparisons between FIG. 12A through FIG. 12I and FIG. 13A through 13I show that the distributions and the relative locations of the three tissues have high consistency. Therefore, the above figures show that the locations of the three tissues respectively classified by automatic segmentation procedure and manual segmentation procedure have high consistency.

Figure 14B:
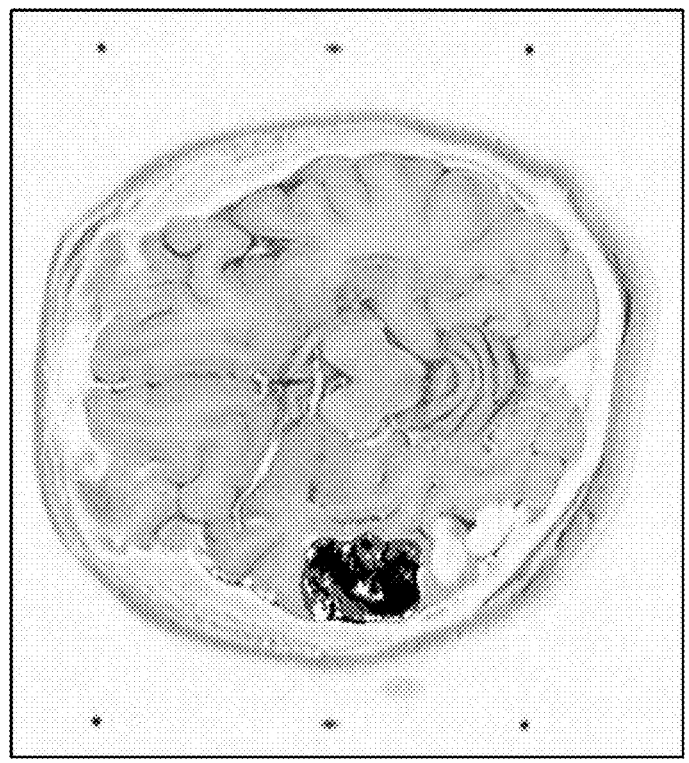
FIG. 14B is the result of the automatic image segmentation of FIG. 14A.
Figure 14A:
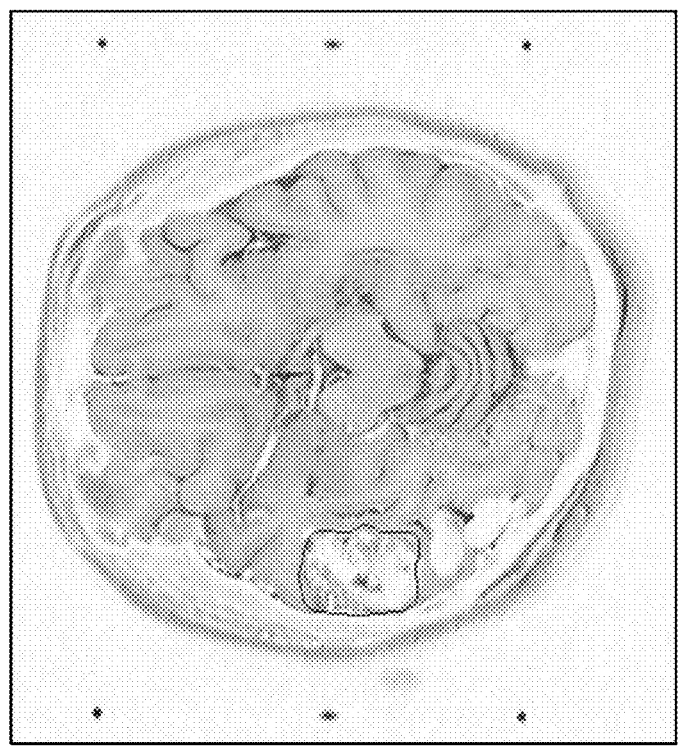
FIG. 14A is a brain MR T2 weighted image according to one example.
Figure 16C:
FIG. 16A through FIG. 16I are respective results of the automatic image segmentation for images of different cross sections of FIG. 15 A through FIG. 15I in accordance with one example.
Figure 16F:
Figure 16I:
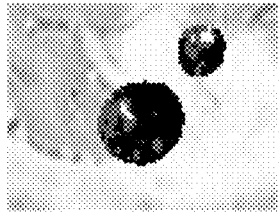
Figure 16B:
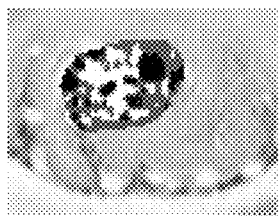
Figure 16E:
Figure 16H:
Figure 16A:
Figure 16D:
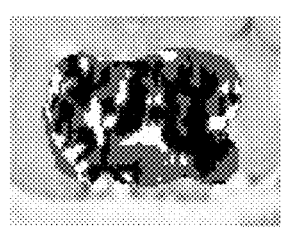
Figure 16G:

Referring to FIG. 14A, it is a brain T2 weighted image according to one example, in which the region surrounded by the black line is an ROI acquired by processes of operation 300. Because the target of the patient of FIG. 14A was located at the edge of the skull, a registered TOF image set was used to extract a brain mask image set and the ROI was within the range of the mask. Consequently, the ROI does not include the skull and the region outside the skull. Please refer to FIG. 14B, which shows results of computer software assisted image segmentation procedure according to the processes of operation 300 for the ROI of FIG. 14A. In FIG. 14B, black color represents nidus, gray color represents brain tissue, and white color represents cerebrospinal fluid.

Referring to FIG. 15A through FIG. 15I, and FIG. 16A through FIG. 16I, the figures show the enlarged target part of FIG. 14A and FIG. 14B. FIG. 15A through FIG. 15I are different cross sections of the target, in which the regions surrounded by the black lines are the ROIs. FIG. 16A through FIG. 16I shows the distribution of three tissues inside the ROIs of FIG. 15A through FIG. 15I, respectively. In the ROIs, black color represents nidus, gray color represents brain tissue, and white color represents cerebrospinal fluid. The calculated results show that in the ROI, the percentage of nidus was 48.4%, the percentage of brain tissue was 39.4%, and the percentage of cerebrospinal fluid was 12.2%.

According to some embodiments of the present disclosure, the algorithm for fully automated analysis includes: converting the dose intensity distribution of a radiotherapy plan into the corresponding three-dimensional special position of a T2 weighted image set by linear interpolation procedure; then selecting an isodose region having a selected radiation dose for determining an ROI; then classifying the voxels inside the ROI according to grayscale values by fuzzy clustering; and calculating the volumes or ratios of the different tissues inside the ROI.

The present disclosure provides methods for analyzing the tissue types within the radiation exposure region of patients. In clinic, morphological measurement of MR images generally is carried out by experienced physicians based on their anatomical knowledge, and different tissue areas are manually delineated in the images. Although manual segmentation method is highly precise, smaller differences in volume may be overlooked. Moreover, it is subjective using manual segmentation procedure; different physicians on the same patient's MR images would have different judgment; difference exists when the same physician examines a same MR image at different time points. Further, the images have problems such as ambiguous, unevenness, etc., due to noise, field offset effect, tissue movement, and local volume effect during imaging taking process. Therefore, compared with automatic segmentation procedure, manual segmentation procedure is slow, poor real-time capable, poor repeatable. Hence, for a lot of image data, using manual segmentation is less competent.

The present disclosure provides algorithms for automatic image analysis by using fuzzy clustering and the characteristics of the grayscale value of different tissues (such as nidus, brain tissue, and cerebrospinal fluid) in MR images.

Compared with manual segmentation procedure performed by physicians, the automatic segmentation procedure has great similarity index, and can quickly, instantly and accurately quantify the ratios of different tissues within the target of radiotherapy.

In clinical applications, precise selection of ROIs in MR images and segmentation of images within ROIs facilitate identification and quantification of tissue types within the region which is actually irradiated with radiation. Embodiments of the present disclosure may be applied to patients receiving radiotherapy, such as patients suffering vascular diseases, neurological diseases, or cancers.

For example, embodiments of the present disclosure may be applied to arterio-Venous malformation (AVM) patients receiving stereotactic radiosurgery. AVM is a kind of congenital brain vascular anomaly. The symptoms of patients with cerebral AVM include hemorrhagic stroke, seizure, and headache. Current treatment of brain AVM includes surgery resection, endovascular embolization, and stereotactic radiosurgery (e.g., Gamma Knife radiosurgery). Among all the treatment options, stereotactic radiosurgery is less invasive and has the lowest acute side-effects, so now it is widely applied in the treatment of AVM, especially for deep seated AVM, small-to-moderate AVM, and AVM located in an eloquent area of a brain. After radiotherapy, the nidus of AVM will be gradually obliterated within 3-5 years; however, radiation may also damage the brain tissue intervening the nidus, and result in focal cerebral edema or radiation necrosis. Most of the radiation-induced brain edema is temporary; however, in a few patients (about 3%), the radiation exposure may cause chronic expanded hematoma or post-radiation cyst several years after radiosurgery. These mass effects to the normal brain tissue outside to the nearby nidus may cause patients suffer permanent neurological deficit or even death. The mechanism of these long-term complications may be related to the radiation exposure to the intervening brain tissue inside the nidus of AVM.

In nidus of cerebral AVMs, normal brain tissue intervenes the vessels of the nidus. In some cerebral AVMs, the vessels distribute densely, so the morphology of the nidi are more compact; in some other cerebral AVMs, the vessels distribute loosely, so the morphology of the nidi are more diffused. The image analysis method of the present disclosure can be used to automatically analyze the ratios of brain tissue inside the nidus. Further, tracking the complications after stereotactic radiosurgery is helpful to understand that whether the ratio of brain tissue is associated with permanent brain radiation injury.

In at least one embodiment, the clinical responses after treatment are followed; through collecting the clinical record, and the volumes or ratios of various tissue components inside the ROI, the correlation between the complications after therapy and the volumes or ratios of brain tissues irradiated can be established; hence the method can be applied to predict or evaluate the risks of complications for patients who underwent radiotherapy. For examples, the method can be applied in evaluating the risks of Gamma Knife radiosurgery for cerebral AVM or other intracranial tumors.

For a radiosurgery plan of brain tumor, sometimes the physicians need to expand the irradiated region because of positioning error or organ movements caused by patients' breath; therefore, more normal tissue is exposed to radiation. By the image analysis method provided in the present disclosure, the correlation between the volumes or ratios of normal tissues within the irradiated region and the complications after therapy can be established; hence, the method can be applied to predict or evaluate the risks of complications for patients with a brain tumor receiving radiotherapy.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A magnetic resonance (MR) imaging analysis method for assessing MR images of a patient who underwent radiotherapy, wherein the radiotherapy is X knife, Cyberknife, Gamma knife, Rapid-arc knife, TomoTherapy, Neutron knife or Proton knife, comprising:
   (a) receiving a first MR image set of the patient, and a dose map of a radiotherapy plan;
   (b) converting radiation dose intensity distribution of the dose map into corresponding spatial positions of the first MR image set by using linear interpolation;
   (c) selecting a radiation dose and a radiation exposure region, wherein the radiation exposure region has radiation intensity being equal to or higher than the radiation dose;
   (d) determining a region of interest (ROI) of the first MR image set via the radiation exposure region;
   (e) classifying voxels inside the ROI into different clusters in accordance with grayscale values of the voxels inside the ROI; and
   (f) calculating volumes or ratios of the different clusters inside the ROI.

2. The MR image analysis method of claim 1, wherein an image type of the first MR image set is T1 weighted image, T2 weighted image, diffusion weighted image, angiography, fractional anisotropy, apparent diffusion coefficient image, radial diffusivity and axial diffusivity image, blood oxygen level dependent image, T1 and T2 parameter-based image, T2 star parameter-based image, or susceptibility parameter-based image.

3. The MR image analysis method of claim 1, wherein step (b) further comprises:
   acquiring radiation doses of positions of various voxels of the first MR image set.

4. The MR image analysis method of claim 1, wherein in step (c), the radiation dose is 30% to 150% dose intensity of the radiotherapy plan.

5. The MR image analysis method of claim 1, wherein step (d) further comprises:
   extracting a mask image set of the patient, and the ROI is located within a corresponding special range of a mask of the mask image set.

6. The MR image analysis method of claim 5, wherein the mask image set of the patient is extracted from the first MR image set.

7. The MR image analysis method of claim 5, wherein the mask image set of the patient is extracted from a second MR image set, and the second MR image set is registered to the first MR image set.

8. The MR image analysis method of claim 5, wherein the mask image set of the patient is extracted from an angiography set of the patient, and the angiography set is registered to the first MR image set.

9. The MR image analysis method of claim 1, wherein step (e) further comprises:
Setting threshold values of the grayscale values of the clusters, and classifying the voxels inside the ROI into the different clusters by the threshold values.

10. The MR image analysis method of claim 1, wherein in step (e), the voxels inside the ROI are classified into the different clusters by fuzzy clustering.

11. The MR image analysis method of claim 1, wherein the different clusters include a normal tissue or a diseased tissue of an organ of sites received the radiotherapy.

12. The MR image analysis method of claim 1, wherein the different clusters comprise nidus, brain tissue, or cerebrospinal fluid.

13. The MR image analysis method of claim 1, further comprising:
performing image segmentation after step (e).

14. The MR image analysis method of claim 13, wherein the image segmentation is an automatic segmentation performed by a computer program.

15. The MR image analysis method of claim 1, wherein the first MR image set is brain T2 weighted image, and the different clusters inside the ROI are nidus, brain tissue, or cerebrospinal fluid.

16. A method for evaluating risks of radiotherapy comprises:
acquiring volumes or ratios of different clusters inside ROIs of patients according to the method of claim 1;
tracking symptoms after the radiotherapy of the patients; and
establishing a correlation between the volumes or the ratios of the different clusters inside the ROIs of the patients and the symptoms.

17. The method for evaluating the risks of radiotherapy of claim 16, wherein the patients have cerebral arterio-venous malformations (AVM), and the different clusters include nidus, brain tissue, or cerebrospinal fluid.

* * * * *